United States Patent
Tymianski

(10) Patent No.: US 10,064,910 B2
(45) Date of Patent: Sep. 4, 2018

(54) COMBINATION THERAPY FOR ISCHEMIA

(75) Inventor: Michael Tymianski, Toronto (CA)

(73) Assignee: NoNO Inc., Toronto, Ontario (CA)

( * ) Notice: Subject to any disclaimer, the term of this patent is extended or adjusted under 35 U.S.C. 154(b) by 0 days.

(21) Appl. No.: 14/128,941

(22) PCT Filed: Jun. 23, 2012

(86) PCT No.: PCT/IB2012/053178
§ 371 (c)(1),
(2), (4) Date: May 21, 2014

(87) PCT Pub. No.: WO2012/176172
PCT Pub. Date: Dec. 27, 2012

(65) Prior Publication Data
US 2014/0248257 A1    Sep. 4, 2014

Related U.S. Application Data

(60) Provisional application No. 61/501,117, filed on Jun. 24, 2011, provisional application No. 61/617,001, filed on Mar. 28, 2012.

(51) Int. Cl.
| | |
|---|---|
| *A61K 38/46* | (2006.01) |
| *A61K 38/10* | (2006.01) |
| *A61K 38/49* | (2006.01) |
| *A61K 38/17* | (2006.01) |

(52) U.S. Cl.
CPC .......... *A61K 38/10* (2013.01); *A61K 38/1787* (2013.01); *A61K 38/49* (2013.01)

(58) Field of Classification Search
None
See application file for complete search history.

(56) References Cited

U.S. PATENT DOCUMENTS

| | | | |
|---|---|---|---|
| 5,922,739 A | 7/1999 | Dargazanli et al. | |
| 2002/0098179 A1* | 7/2002 | Brearley | A61K 38/17 424/94.64 |
| 2005/0059597 A1* | 3/2005 | Tymianski | A61K 38/1709 514/17.3 |
| 2007/0123567 A1 | 5/2007 | Maxwell et al. | |

(Continued)

FOREIGN PATENT DOCUMENTS

| | | |
|---|---|---|
| CA | 2524573 A1 | 11/2004 |
| WO | WO 08/008348 A2 | 1/2008 |

(Continued)

OTHER PUBLICATIONS

Saver, Neurology 57(Suppl 2): S58-S60 (2001).*

(Continued)

*Primary Examiner* — Erin M. Bowers
(74) *Attorney, Agent, or Firm* — Alston & Bird LLP

(57) ABSTRACT

The invention provides a combination treatment for ischemia conditions in or otherwise affecting the CNS, such as stroke. The treatment invoices administration of a PSD-95 inhibitor and performing reperfusion therapy (e.g. by administration of tPA). Administration a PSD-95 inhibitor in combination with reperfusion therapy increases the efficacy of the reperfusion therapy and/or slows the decline in efficacy of reperfusion therapy with time after onset of ischemia thus extending the window in which reperfusion therapy can be administered.

28 Claims, 11 Drawing Sheets
Specification includes a Sequence Listing.

(56) References Cited

U.S. PATENT DOCUMENTS

| | | | |
|---|---|---|---|
| 2009/0258821 A1* | 10/2009 | Cerami | A61K 38/1816 514/1.1 |
| 2012/0208764 A1 | 8/2012 | Tymianski | |
| 2012/0269733 A1 | 10/2012 | Tymianski et al. | |
| 2013/0156704 A1 | 6/2013 | Tymianski | |
| 2015/0202253 A1 | 7/2015 | Tymianski et al. | |
| 2016/0228499 A1 | 8/2016 | Tymianski | |

FOREIGN PATENT DOCUMENTS

| | | |
|---|---|---|
| WO | WO 08/014917 A1 | 2/2008 |
| WO | WO 08/109010 A1 | 9/2008 |
| WO | WO 10/144721 A2 | 12/2010 |
| WO | WO 12/176172 A2 | 12/2012 |
| WO | WO 13/088382 A1 | 6/2013 |

OTHER PUBLICATIONS

Lantos et al., "CT perfusion for stroke: should you use it?", http://www.physicianspractice.com/ct/ct-perfusion-stroke-should-you-use-it/page/0/2, published Nov. 3, 2010, accessed Oct. 28, 2015.*
ClinicalTrials.gov Identifier NCT00728182, "Evaluating Neuroprotection in Aneurysm Coiling Therapy (ENACT)," ClinicalTrials.gov, Full Text View, U.S. National Institutes of Health, Aug. 1, 2008. [Retrieved from the Internet Feb. 18, 2015: <URL: https://clinicaltrials.gov/ct2/show/study/NCT00728182>].
"Abstracts of the 46th Annual Congress of the Canadian Neurological Sciences Federation," Can J Neurol Sci, 38(3):1-94, (2011).
"Novel Therapeutic Compounds for Subarachnoid Hemorrhage," Cognosci, Inc., 3 pages, (2007). [Retrieved from the Internet May 13, 2014: <URL: http://www.cognosci.com/documents/sah_white_paper.pdf>].
"Species Dosage Conversion Factors," National Cancer Institute (NCI), Frederick National Laboratory for Cancer Research, Laboratory Animal Sciences Program (LASP), Animal Care and Use Committee (ACUC) Guidelines, ACUC 42.00, 1 pages, (2007). [Retrieved from the Internet Jul. 15, 2014: <URL: https://ncifrederick.cancer.gov/Lasp/Acuc/Frederick/Media/Documents/ACUC42.pdf>].
"Subarachnoid Hemorrhage," The Free Online Medical Dictionary, 7 pages, (2001). [Retrieved from the Internet Aug. 6, 2013: <URL: http://medical-dictionary.thefreedictionary.com/subarachnoid+hemorrhage>].
Aarts et al., "Treatment of Ischemic Brain Damage by Perturbin NMDA Receptor-PSD-95 Protein Interactions," Science, 298(5594):846-850, (2002).
Ardizzone et al., "Src kinase inhibition improves acute outcomes after experimental intracerebral hemorrhage," Stroke, 38:1621-1625, (2007).
Bang et al., "Specific DWI lesion patterns predict prognosis after acute ischaemic stroke within the MCA territory," J Neurol Neurosurg Psychaiatry, 76:1222-1228, (2005).
Bratane et al., "Neuroprotection by freezing ischemic penumbra evolution without cerebral blood flow augmentation with a post-synaptic density-95 protein inhibitor," Stroke, 42(11):3265-3270, (2011).
Brooks et al., "Frequency of thromboembolic events associated with endovascular aneurysm treatment: retrospective case series", Journal of Neurosurg, 108:1095-1100, (2008).
Cook al., "Treament of stroke with a PSD-95 inhibitor in the gyrencephalic primate brain," Nature, 483(7388):213-217, (2012).
Cronqvist et al., "Diffusion and perfusion MRI in patients with ruptured and unruptured intracranial aneurysms treated by endovascular coiling: complications, procedural results, MR findings and clinical outcome," Neuroradiology, 47:855-873, (2005).
Cui et al. "PDZ protein interactions underlying NMDA receptor-mediated excitotoxicity and neuroprotection by PSD-95 inhibitors," J. Neurosci., 27(37):9901-9915, (2007).

Davis et al., "Termination of Acute Stroke Studies Involving Selfotel Treatment," The Lancet, 349:32-32, (1997).
Donnan et al., "How to make better use of thrombolytic therapy in acute ischemic stroke," Nat Rev Neurol., 7(7): 400-409, (2011).
EPO Application No. 10786859.8, Supplementary European Search Report and European Search Opinion dated Apr. 30, 2014.
EPO Application No. EP 12802409.8, Supplementary European Search Report and European Search Opinion dated Nov. 12, 2014.
Fan et al., "N-Methyl-D-aspartate receptor subunit- and neuronal-type dependence of excitotoxic signaling through poet-synaptic density 95," Journal of Neurochemistry, 115(4):1045-1056, (2010).
Fan, et al. "Interaction of postsynaptic density protein-95 with NMDA receptors influences excitotoxicity in the yeast artificial chromosome mouse model of Huntington's disease," J. Neurosci,. 29(35):10928-10938, (2009).
Florio, et al., "Disruption of nNOS-PSD95 Protein-protein Interaction Inhibits Acute Thermal Hyperalgesia and Chronic Mechanical Allodynia in Rodents", Brit. J. Pharmacol., 158(2):494-506, (2009).
Germano et al., "NMDA receptor antagonist felbamate reduces behavioral deficits and blood-brain barrier permeability changes after experimental subarachnoid hemorrhage in the rat," J Neurotrauma, 24(4):732-744, (2007).
Haley et al., "A randomized, double-blind, vehicle-controlled trial of tirilazad mesylate in patients with aneurysmal subarachnoid hemorrhage: a cooperative study in North America," J Neurosurg, 86(3):467-474, (1997). Abstract Only.
Herce, et al., "Molecular dynamics simulations suggest a mechanism for translocation of the HIV-1 TAT peptide across lipid membranes," Proc. Natl. Acad. Sci. U. S. A., 104(52):20805-20810, (2007).
Hill et al., "Safety and efficacy of NA-1 in patients with iatrogenic stroke after endovascular aneurysm repair (ENACT): a phase 2, randomised, double-blind, placebo-controlled trial," The Lancet Neurology, 11(11):942-950, (2012).
Horn et al., "Very Early Nimodipine Use in Stroke (VENUS): A Randomized, Double-Blind, Placebo-Controlled Trial," Stroke, 32:461-465, (2001).
Kaufmann et al., "Complications of Diagnostic Cerebral Angiography: Evaluation of 19 826 Consecutive Patients", Radiology, 243(3):812-819, (2007).
Kleckner et al., "Subtype-Selective Antagonism of N-Methyl-o-Aspartate Receptors by Felbamate: Insights into the Mechanism of Action," JPET, 289(2):898-894, (1999).
Kusaka et al., "Signaling pathways for early brain injury after subarachnoid hemorrhage," J Cerebral Blood Flow & Metabolism, 24:916-925, (2004).
Lanzino et al., "Double-blind, randomized, vehicle-controlled study of high-dose tirilazad mesylate in women with aneurysmal subarachnoid hemorrhage. Part II. A Cooperative study in North America," J Neurosurg, 90(6):1018-1024 , (199). Abstract Only.
Lees, "Cerestat and other NMDA antagonists in ischemic stroke," Neurology, 49(Suppl 4):S66-S69, (1997).
Li, "Pharmacologically Induced Histamine Release: Sorting Out Hypersensitivity Reactions to Opioids," Publication, 35(4):1,14-16, (2006).
Martel, et al., "Inhibiting pro-death NMDA receptor signaling dependent on the NR2 PDZ ligand may not affect synaptic function or synaptic NMDA receptor signaling to gene expression," Channels (Austin), 3(1):12-15, (2009).
Miyazawa et al., "Effect of mild hypothermia on focal cerebral ischemia. Review of experimental studies," Neurol Res, 25(5):457-464, (2003). Abstract Only.
Morgan et al., "Chapter 9: Neuromuscular Blocking Agents," Clinical Anesthesiology, 4th Edition, McGraw-Hill Companies, Inc., 32 pages, (2006). [Retrieved from the Internet Jan. 7, 2014: <URL: http://bentollenaar.com/_MM_Book/Ch.9.htm>].
Nelson et al., "Myristoyl-based transport of peptides into living cells," Biochem, 46(51):14771-14781, (2007).
Sam "Differential protein interactions of nmda receptor NR2 subunits" Doctoral thesis; University of Toronto,. (2010).
Sena et al., "Systematic Review and Meta-Analysis of the Efficacy of Tirilazad in Experimental Stroke," Publication,Stroke, 38:388-

(56) References Cited

OTHER PUBLICATIONS 394, (2007). Retrieved from the Internet Dec. 3, 2014: <URL: http://stroke.ahajournals.org/content/38/2/388/>].
Soriano, et al., "Specific targeting of pro-death NMDA receptor signals with differing reliance on the NR2B PDZ ligand," J. Neurosci., 28(42):10696-1071015, (2008).
Sturgill et al., "distinct domains within psd-95 mediate synaptic incorporation, stabilization, and activity-dependent trafficking," J neurosci, 29(41):12845-12854, (2009).
Sun, et al. "Effectiveness of PSD95 inhibitors in permanent and transient focal ischemia in the rat," Stroke, 39(9):2544-2553, (2008).
Todd et al., "Mild Intraoperative Hypothermia during Surgery for Intracranial Aneurysm," N Engl J Med, 352:135-145, (2005).
U.S. Appl. No. 13/377,523, Final Office Action dated Jan. 15, 2014.
U.S. Appl. No. 13/377,523, Non-Final Office Action dated Apr. 29, 2013.
U.S. Appl. No. 13/377,523, Notice of Allowance and Examiner Initiated Interview Summary dated Sep. 12, 2014.
U.S. Appl. No. 13/774,053, Final Office Action dated Jan. 15, 2014.
U.S. Appl. No. 13/774,053, Non-Final Office Action and Examiner Initiated Interview Summary dated Jun. 3, 2014.
U.S. Appl. No. 13/774,053, Non-Final Office Action dated Aug. 14, 2013.
Westermaier, "Neuroprotective Treatment Strategies for Delayed Cerebral Ischemia after Subarachnoid Hemorrhage—Review of Literature and Future Prosepcts," J Neural Neurophysiol, 5(1):1-8, (2013).
WIPO Application No. PCT/IB2012/053178, PCT International Preliminary Report on Patentability dated Jan. 9, 2014.
WIPO Application No. PCT/IB2012/053178, PCT International Search Report and Written Opinion of the International Searching Authority dated Oct. 10, 2012.
WIPO Application No. PCT/IB2012/057259, PCT International Preliminary Report on Patentability dated Jun. 26, 2014.
WIPO Application No. PCT/IB2012/057259, PCT International Search Report and Written Opinion of the International Searching Authority dated Apr. 12, 2013.
WIPO Application No. PCT/US2010/038200, International Search Report and Written Opinion of the International Searching Authority, dated Jun. 10, 2010.
WIPO Application No. PCT/US2010/038200, PCT International Preliminary Report on Patentability dated Dec. 22, 2011.
Zaleska et al., "The development of stroke therapeutics: Promising mechanisms and translational challenges," Neuropharmacology, 56:329-341, (2009).
"Activase (Alteplase) Full Prescribing Information ," Genentech, Inc., 16 pages, (2015).
EPO Application No. 12857611.3, Supplementary European Search Report and European Search Opinion dated Aug. 21, 2015.
Grasso et al., "An overview of new pharmacological treatments for cerebrovascular dysfunction after experimental subarachnoid hemorrhage," Brain Research Reviews, 44(1):49-63, (2004).
Krams et al., "Acute Stroke Therapy by Inhibition of Neutrophils (ASTIN), An Adaptive Dose-Response Study of UK-279,276 in Acute Ischemic Stroke," Stroke, 34:2543-2548, (2003).
U.S. Appl. No. 13/774,053, Notice of Allowance dated Sep. 3, 2015.
U.S. Appl. No. 14/597,166, Non-Final Office Action dated Jan. 14, 2015.
Fisher et al., "Current Concepts of the Ischemic Penumbra: Introduction ," Stroke, 35:2657-2658, (2004).
Gerraty et al., "Examining the Lacunar Hypothesis With Diffusion and Perfusion Magnetic Resonance Imaging," Stroke, 33:2019-2024, (2002).
Saver et al., "Alteplase for ischaemic stroke—much sooner is much better," www.thelancet.com, 375:1667-1668, (2010).
U.S. Appl. No. 14/597,166, Final Office Action dated Sep. 22, 2016.
Wong et al., "Early changes in physiological variables after stroke," Ann Indian Acad Neurol, 11(4): 207-220, (2008).
Applegate et al. (eds.), "Large Animal Stroke Models vs. Rodent Stroke Models, Pros and Cons, and Combination?," Brain Edema XVI: Translate Basic Science into Clinical Practice, Acta Neurochirurgica Supplement, 121:77-81, doi: 10.10071978-3-319-18497-5_13, (2016).
Bassand et al., "Differential interaction of the tSXV motifs of the NR1 and NR2A NMDA receptor subunits with PSD-95 and SAP97," Eur. J. Neuroscience, 11:2031-2043, (1999).
Cook, "effectiveness of NA-1, a PSD-95 inhibitor, in a non-human primate model of embolic stroke," Front Neurosci Conference, (2009). Abstract only.
Furuyashiki et al, "Citron, a Rho-Target, Interacts with PSD-95/SAP-90 a Glutamatergic Synapses in the Thalamus," Journal of Neuroscience, 19(1):109-118, (1999).
Hoh, "Computed tomographic demonstrated infarcts after surgical and endovascular treatment of aneurysmal subarachnoid hemorrhage," Acta Neurochir (Wien), 146:1177-1183, (2004).
Jimbo et al., "Cerebrovascular Spasm After Subarachnoid Bleeding," Comprehensive Clinical, 60(9):1943-1944, (2011).
Korneau, "Domain Interaction Between NMDA Receptor Subunits and the Postsynaptic Density Protein PSD-95," Science 269:1737-4040, (1995).
Leiva-Salinas, "Imaging of Ischemic Stroke," Neuroimaging Clin N Am, 20(4):455-468, (2010).
Niethammer et al, "CRIPT, a Novel Postsy naptic Protein thatBinds to the Third PD ZDo main ofPSD-95/Sa P90," Neuron, 20:693-707, (1998).
Tymianski, "Can Molecular and Cellular Neuroprotection Be Translated Into Therapies for Patients?: Yes, But Not the Way We Tries It Before" Stroke, 41:S87-S90, (2010).
U.S. Appl. No. 14/597,166 , Notice of Allowance dated Nov. 18, 2016.
U.S. Appl. No. 14/597,166, Notice of Allowance dated Dec. 13, 2016.
U.S. Appl. No. 14/965,694, Non-Final Office Action dated Jun. 21, 2017.
U.S. Appl. No. 14/965,694, Requirement for Restriction/Election dated Jan. 30, 2017.
"Tissue Plasminogen Activator for Acute Ischemic Stroke," N Engl J Med, 333:1581-1587, (1995). [Author Unknown].
Cook et al., "Extenting the therapeutic window for reperfusion after stroke in non-human primates using a PSD-95 inhibitor," Canadian Journal of Neurological Sciences, 38(Suppl.1):S15-S15, Abstract No. C-05, (2011).
Ehrenreich et al., "Recombinant Human Erythropoietin in the Treatment of Acute Ischemic Stroke," Stroke, 40:e647-e656, (2009).
Goyal et al., "Randomized Assessment of Rapid Endovascular Treatment of Ischemic Stroke," N Engl J Med, 12 pages, doi: 10.1056/NEJMoa1414905, (2015).
Kamiya et al., "Future neuroprotective strategies in the post-thrombolysis era—neurovascular unit protection and vascular endothelial protection," Clin Neurol, 51(5):305-315, (2011). Abstract only.
Rha et al., "The Impact of Recanalization on Ischemic Stroke Outcome—A Meta-Analysis," Stroke, 38:967-973, (2007).

* cited by examiner

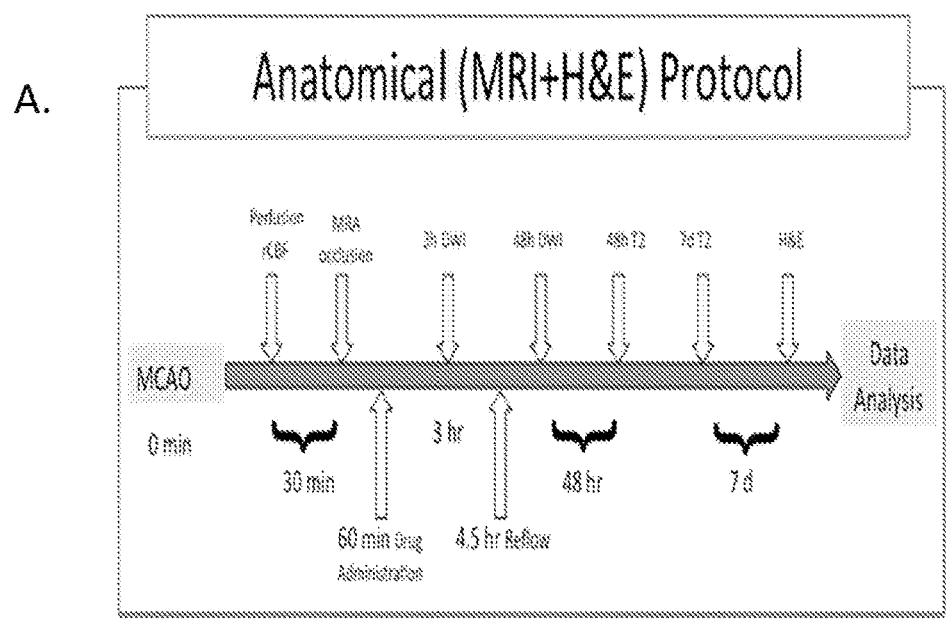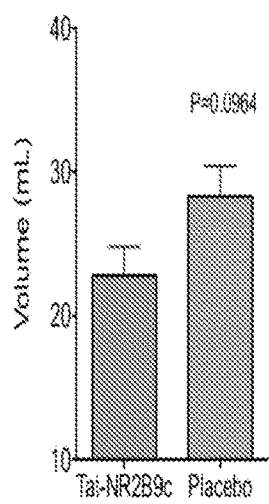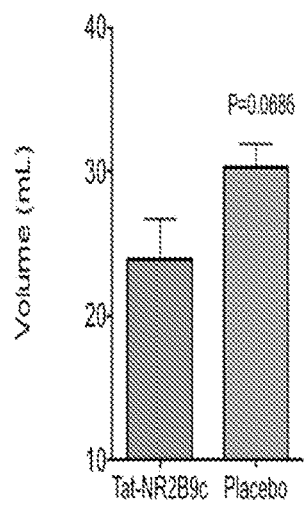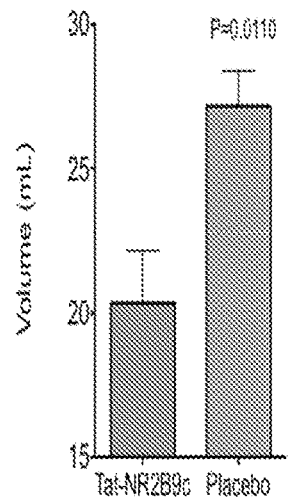
FIG 1A-D

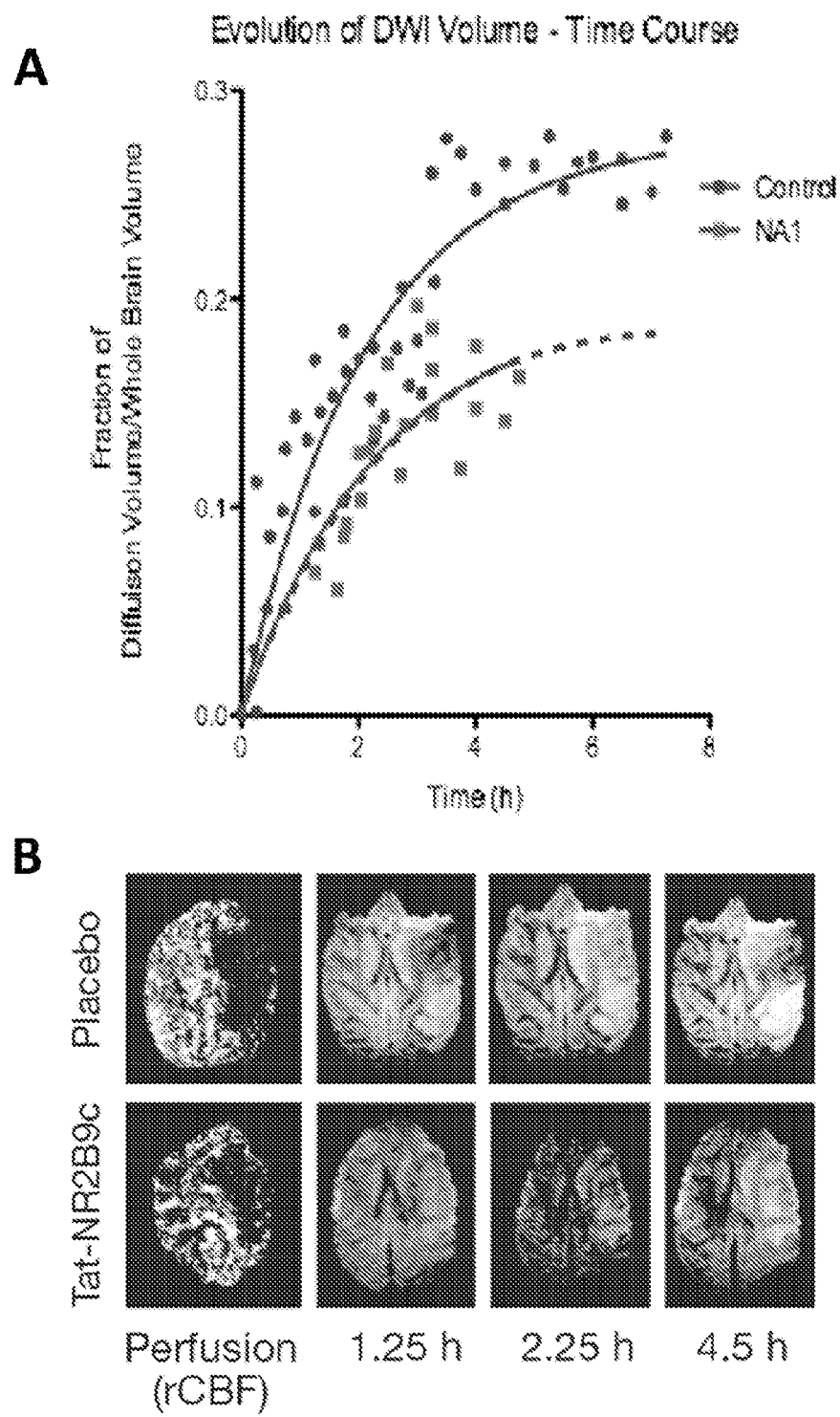
FIG 2A,B

COMBINATION THERAPY FOR ISCHEMIA

CROSS REFERENCE OF RELATED APPLICATION

This application is the US national stage of PCT/IB2012/053178 filed Jun. 23, 2012, which claims priority to U.S. 61/501,117 filed Jun. 24, 2011 and U.S. 61/617,001 filed Mar. 28, 2012, each of which is incorporated by reference in its entirety for all purposes.

INCORPORATION BY REFERENCE OF SEQUENCE LISTING

The sequence listing in file 440586SEQLIST.TXT was created Mar. 13, 2014, and is 18 kilobytes. This sequence listing is hereby incorporated by reference.

BACKGROUND

Ischemic stroke is a common cause of death and serious disability and is usually caused by a blockage in a blood vessel leading to or within the intracranial cavity and/or brain. Few effective treatments are available. One treatment consists of removing the blockage within the blood vessel in question. Other treatments consist of altering perfusion pressures within the brain by increasing blood pressure to the brain. Blockage of blood vessels can be removed using a range of mechanical devices, or using "clot busting agents" which are delivered intravenously or intra-arterially. Among such clot busting agents is Tissue plasminogen factor (tPA), a thrombolytic agent that is administered to some stroke subjects to dissolve emboli causing the ischemia and thus restore blood flow to the brain, and recombinant tPA's such as Alteplase, reteplase and tenecteplase. Other thrombolytic drugs that break down clots include streptokinase, urokinase and desmotaplase. Among mechanical reperfusion devices, there are intra-arterial catheters, balloons, stents, and various clot retrieval devices, such as the Penumbra System Reperfusion Cather. Among treatments that alter perfusion pressures in the brain are devices that increase the arterial pressure in the brain, such as balloons that can be inflated in the extra-cerebral arteries such as the aorta thereby diverting blood flow from other body areas and increasing brain arterial perfusion, such as the CoAxia NeuroFlow™ catheter device. Collectively, these strategies can be considered as medical and mechanical agents that enhance brain perfusion on or after the onset of cerebral ischemia (hereafter collectively "reperfusion therapies").

Although tPA and other reperfusion therapies administered soon after onset of ischemia are effective in reducing death or disability from ischemic stroke, less than about 3% of subjects presenting with stroke are treated with tPA or other reperfusion therapies. The low usage of tPA and other reperfusion therapies is due in part to the risk of death if administered to a patient who is having or who is at an elevated risk for sustaining a brain hemorrhage. Stroke can be the result of ischemia or hemorrhage. Too often, the time required to bring a subject to a hospital, reach an initial diagnosis and perform a brain scan to distinguish between ischemic and hemorrhagic stroke would place a subject outside the window in which tPA or other reperfusion therapies can be effective. Thus, many ischemic stroke subjects, who could benefit from tPA or other reperfusion therapies, do not receive such treatment.

A different form of treatment for stroke and related conditions is now in clinical trials (see WO 2010144721 and Aarts et al., Science 298, 846-850 (2002)). This treatment uses Tat-NR2B9c (NA-1), an agent that inhibits PSD-95, thus disrupting binding to N-methyl-D-aspartate receptors (NMDARs) and neuronal nitric oxide synthases (nNOS) and reducing excitotoxicity induced by cerebral ischemia. Treatment reduces infarction size and functional deficits.

BRIEF DESCRIPTION OF THE FIGURES

FIGS. 1A, B, C, and D: Description of the protocol for dosing non-human primates (NHPs; A), and graphs of the resulting diffusion volumes on MRI indicating areas of damage. B. DWI MRI 48 hours after the onset of a 4.5 hour stroke. C. T2 volume 48 house after the onset of a 4.5 hour stroke. D. T2 volume 7 days after the onset of a 4.5 hour stroke.

FIGS. 2A, B. A. Animals were subjected to 4.5 hour MCAO and treated within 5 min with Tat-NR2B9c or placebo. Time course of increase in DWI hyperintensity after MCAO in treated and control animals. B. Perfusion and MRI images of brain at different time points.

SUMMARY OF THE CLAIMED INVENTION

Figure 3:
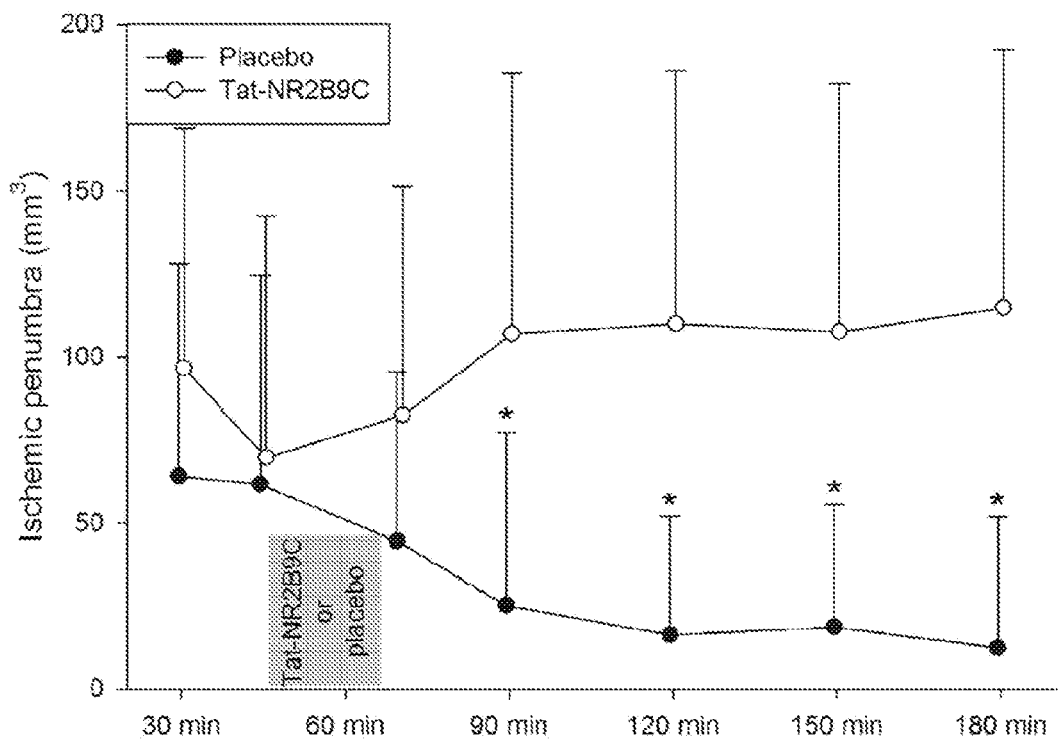
FIG. 3. Temporal evolution of penumbra mismatch in placebo or Tat-NR2B9c animals.

The invention provides a method of treating a damaging effect of ischemia on the central nervous system, comprising administering a PSD-95 inhibitor to a subject having or at risk of ischemia, and performing reperfusion therapy on the subject, wherein the PSD95-inhibitor and reperfusion therapy treat a damaging effect of the ischemia on the central nervous system of the subject. Optionally, the PSD-95-inhibitor is administered before reperfusion therapy is performed. Optionally, the PSD-95-inhibitor is administered to a subject at risk of ischemia before onset of ischemia and the reperfusion therapy is performed after onset of ischemia. Optionally, the PSD-95-inhibitor is administered and reperfusion therapy is performed after onset of ischemia. In some methods, the ischemia is cerebral ischemia. In some methods, the subject has a stroke. In some methods, the ischemia is cardiac, pulmonary or major limb ischemia affecting the central nervous system by inhibiting blood flow to or from the CNS. In some methods, the subject is tested for presence of cerebral ischemia and/or absence of cerebral hemorrhage between administration of the agent and performance of the reperfusion therapy. In some methods, the subject is assessed for presence or risk of hemorrhage between administering the agent and performance of the reperfusion therapy. In some methods, the assessment includes performing a PET scan, CAT scan, MRI or reviewing the subject's medical history or the use of one or more biomarkers providing an indication of ischemia. In some methods, the PSD-95-inhibitor is a peptide. In some methods, the agent is NA-1 (Tat-NR2B9c). In some methods, the reperfusion is performed by administering a thrombolytic agent. In some methods, the thrombolytic agent is a plasminogen activator. In some methods, the thrombolytic agent is tPA. In some methods, the reperfusion therapy is mechanical reperfusion. In some methods, the reperfusion therapy is performed more than 3 hours after onset of ischemia. In some methods, the reperfusion therapy is performed more than 4.5 hours after onset of ischemia. In some methods, the reperfusion therapy is performed more than 4.5 hours and less than 24 hours after onset of ischemia. In some methods, the reperfusion therapy is performed after determining the subject qualifies for reperfusion based on lack of a completed infarction, an ischemic penumbra and lack of hemorrhage as shown by CT, MRI or PET analysis. In some methods, the reperfusion therapy is performed at least 12 or at least 24 hours after onset of ischemia. In some methods, the reperfusion therapy is performed 275-690 minutes after onset of ischemia. In some methods, the interval between administering PSD-95 and reperfusion therapy can be 30 min to 6 hr. In some methods, a thrombolytic agent is administered by localized administration to a site of impaired blood flow. In any of the above methods, the peptide or other agent can be linked to an internalization peptide or lipidated thereby facilitating passage of the peptide across a cell membrane or the blood brain barrier. Some peptides or other agents are myristoylated. Peptides are preferably myristoylated at the N-terminus.

The invention further provides a method of treating a subject population presenting sign(s) and/or symptom(s) of ischemia, comprising administering a PSD-95 inhibitor to the subjects; wherein the subjects are analyzed for unacceptable risk of side effects of reperfusion therapy, and subjects without unacceptable risk of side effects receive reperfusion therapy and subjects with unacceptable risk of side effects do not receive reperfusion therapy. In some methods, the analysis of unacceptable risk of side effects includes analysis for presence or risk of hemorrhage. In some methods, the subjects present sign(s) and/or symptom(s) of stroke and the analysis includes performing a brain scan that distinguishes ischemic stroke and hemorrhagic stroke and subjects having ischemic stroke receive the reperfusion therapy and subjects having hemorrhagic stroke do not.

The invention provides an agent that inhibits PSD-95 binding to NMDAR 2B or other NMDAR 2 subunit(s) for use in treating a damaging effect of ischemia on the central nervous system in a subject also receiving reperfusion therapy, wherein the reperfusion therapy and agent treat damaging effects of the ischemia on the central nervous system.

The invention further provides an agent or device for use in reperfusion therapy in a subject also receiving an agent that inhibits PSD-95 binding to NMDAR 2B, 2A or nNOS wherein the reperfusion therapy and the agent treat a damaging effect of the ischemia on the central nervous system. Optionally, the device is a coil, stent, balloon (e.g., an intra-aortic balloon, pump), catheter. Optionally, the agent is a thrombolytic, vasodilator or hypertensive agent.

DEFINITIONS

A "chimeric peptide" means a peptide having two component peptides not naturally associated with one another joined to one another as a fusion protein or by chemical linkage.

A "fusion" protein or polypeptide refers to a composite polypeptide, i.e., a single contiguous amino acid sequence, made up of sequences from two (or more) distinct, heterologous polypeptides which are not normally fused together in a single polypeptide sequence.

The term "PDZ domain" refers to a modular protein domain of about 90 amino acids, characterized by significant sequence identity (e.g., at least 60%) to the brain synaptic protein PSD-95, the *Drosophila* septate junction protein Discs-Large (DLG), and the epithelial tight junction protein ZO1 (Z01). PDZ domains are also known as Discs-Large homology repeats ("DHRs") and GLGF (SEQ ID NO:7) repeats. PDZ domains generally appear to maintain a core consensus sequence (Doyle, D. A., 1996, Cell 85: 1067-76). Exemplary PDZ domain-containing proteins and PDZ domain sequences disclosed in U.S. application Ser. No. 10/714,537, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 9, 10, 12, 14 or 16 residues), forms such a molecular complex. The molecular complex can be observed in vitro using the "A assay" or "G assay" described, e.g., in US 20060148711, or in vivo.

The term "NMDA receptor," or "NMDAR," refers to a membrane associated protein that is known to interact with NMDA including the various subunit forms described below. Such receptors can be human or non-human (e.g., mouse, rat, rabbit, monkey).

A "PL motif" refers to the amino acid sequence of the C-terminus of a PL protein (e.g., the C-terminal 3, 4, 5, 6, 7, 8, 9, 10, 12, 14, 16, 20 or 25 contiguous residues) ("C-terminal PL sequence") or to an internal sequence known to bind a PDZ domain ("internal PL sequence").

A "PL peptide" is a peptide of comprising or consisting of, or otherwise based on, a PL motif that specifically binds to a PDZ domain.

The terms "isolated" or "purified" means that the object species (e.g., a peptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species. The term isolated or purified does not necessarily exclude the presence of other components intended to act in combination with an isolated species. For example, an internalization peptide can be described as isolated notwithstanding that it is linked to an active peptide.

A "peptidomimetic" refers to a synthetic chemical compound which has substantially the same structural and/or functional characteristics of a peptide consisting of natural amino acids. The peptidomimetic can contain entirely synthetic, non-natural analogues of amino acids, or can be a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. In a peptidomimetic of a chimeric peptide comprising an active peptide and an internalization peptide, either the active moiety or the internalization moiety or both can be a peptidomimetic.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

Excitotoxicity is the pathological process by which neurons are damaged and killed by the overactivation of receptors for the excitatory neurotransmitter glutamate, such as the NMDA receptors, e.g., NMDA receptors bearing the NMDAR 2B subunit.

The term "subject" includes humans and veterinary animals, such as mammals, as well as laboratory animal models, such as mice or rats used in preclinical studies.

The term "agent" includes any compound including compounds with or without pharmaceutical activity, natural compounds, synthetic compounds, small molecules, peptides and peptidomimetics. A PSD-95 inhibitor is an agent that inhibits PSD-95 as further described below.

The term "pharmacologic agent" means an agent having a pharmacological activity. Pharmacological agents include compounds that are known drugs, compounds for which pharmacological activity has been identified but which are undergoing further therapeutic evaluation in animal models or clinical trials. A chimeric agent comprises a pharmacologic agent linked to an internalization peptide. An agent can be described as having pharmacological activity if it exhibits an activity in a screening system that indicates that the active agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

A tat peptide means a peptide comprising or consisting of GRKKRRQRRR (SEQ ID NO:1), in which no more than 5 residues are deleted, substituted or inserted within the sequence, which retains the capacity to facilitate uptake of a linked peptide or other agent into cells. Preferably any amino acid changes are conservative substitutions. Preferably, any substitutions, deletions or internal insertions in the aggregate leave the peptide with a net cationic charge, preferably similar to that of the above sequence. Such can be accomplished by not substituting or deleting a significant number of R and K residues. The amino acids of a tat peptide can be derivatized with biotin or similar molecule to reduce an inflammatory response.

Co-administration of a pharmacological agents means that the agents are administered sufficiently close in time for detectable amounts of the agents to present in the plasma simultaneously and/or the agents exert a treatment effect on the same episode of disease or the agents act co-operatively, or synergistically in treating the same episode of disease. For example, an anti-inflammatory agent acts cooperatively with an agent including a tat peptide when the two agents are administered sufficiently proximately in time that the anti-inflammatory agent can inhibit an anti-inflammatory response inducible by the internalization peptide.

Statistically significant refers to a p-value that is <0.05, preferably <0.01 and most preferably <0.001.

An episode of a disease means a period when signs and/or symptoms of the disease are present interspersed by flanked by longer periods in which the signs and/or symptoms or absent or present to a lesser extent.

DETAILED DESCRIPTION

I. General

The present invention provides a combination treatment for ischemia in or otherwise affecting the CNS, such as ischemic stroke. The treatment involves administration of a PSD95 inhibitor and performing a reperfusion therapy (e.g., by administration of tPA or another thrombolytic agent, or by using a mechanical device to increase blood flow to the affected CNS area). In conventional use of tPA and other reperfusion therapies, the efficacy declines with increasing time from onset of ischemia and the potential for hemorrhagic side effects increases. Thus, in the case of tPA, this thrombolytic strategy is considered ineffective after about 3-4.5 hr from onset of ischemia. The invention is based in part on the insight that administering a PSD95 inhibitor in combination with a reperfusion therapy increases the efficacy of the reperfusion therapy and/or slows the decline in efficacy of tPA or other reperfusion therapies with time after onset of ischemia thus extending the window in which tPA or other reperfusion therapies can be administered.

Whereas tPA and other reperfusion therapies can be safely administered only to stroke subjects known to have ischemic stroke, the PSD-95 inhibitor can be administered safely to any stroke or possible stroke subject, irrespective whether the subject has ischemic or hemorrhagic stroke and irrespective whether the subject has suffered a stroke at all. By administering the PSD-95 inhibitor, there is more time available to perform a brain scan or any other diagnostic test in order to determine presence of ischemic stroke, and then administer tPA or another reperfusion therapy if appropriate. Thus, more subjects with ischemic stroke can benefit from tPA or other reperfusion therapies and at the same time benefit from treatment with a PSD-95 inhibitor.

II. Agents Inhibiting PSD-95

PSD-95 inhibitors inhibit interaction between PSD-95 and one or more NMDARs (e.g., 2A, 2B, 2C or 2D) or nNOS (e.g., Swiss-Prot P29475). Inhibition can be, for example, the result of specific binding of the inhibitor to PSD-95. Such agents are useful for reducing one or more damaging effects of stroke and other neurological conditions mediated at least in part by NMDAR excitotoxicity. Such agents include peptides having an amino acid sequence including or based on the PL motif of a NMDA Receptor or PDZ domain of PSD-95. Such peptides can also inhibit interactions between PSD-95 and nNOS and other glutamate receptors (e.g., kainite receptors or AMPA receptors), such as KV1-4 and GluR6. Preferred peptides inhibit interaction between PDZ domains 1 and 2 of postsynaptic density-95 protein (PSD-95)(human amino acid sequence provided by Stathakism, Genomics 44(1):71-82 (1997)) and the C-terminal PL sequence of one or more NMDA Receptor 2 subunits including the NR2B subunit of the neuronal N-methyl-D-aspartate receptor (Mandich et al., Genomics 22, 216-8 (1994)). NMDAR2B has GenBank ID 4099612, a C-terminal 20 amino acids FNGSSNGHVYEKLSSIESDV (SEQ ID NO:11) and a PL motif ESDV (SEQ ID NO:12). Preferred peptides inhibit the human forms of PSD-95 and human NMDAR receptors. However, inhibition can also be shown from species variants of the proteins. A list of NMDA and glutamate receptors that can be used appears below:

TABLE 1

NMDA Receptors With PL Sequences

| Name | GI or Acc# | C-terminal 20mer sequence | C-terminal 4mer sequence | PL? | internal PL ID |
|---|---|---|---|---|---|
| NMDAR1 | 307302 | HPTDITGPLNLSDPSVSTVV (SEQ ID NO: 13) | STVV (SEQ ID NO: 27) | X | AA216 |
| NMDAR1-1 | 292282 | HPTDITGPLNLSDPSVSTVV (SEQ ID NO: 13) | STVV (SEQ ID NO: 27) | X | AA216 |
| NMDAR1-4 | 472845 | HPTDITGPLNLSDPSVSTVV (SEQ ID NO: 13) | STVV (SEQ ID NO: 27) | X | AA216 |
| NMDAR1-3b | 2343286 | HPTDITGPLNLSDPSVSTVV (SEQ ID NO: 13) | STVV (SEQ ID NO: 27) | X | AA216 |
| NMDAR1-4b | 2343288 | HPTDITGPLNLSDPSVSTVV (SEQ ID NO: 13) | STVV (SEQ ID NO: 27) | X | AA216 |
| NMDAR1-2 | 11038634 | RRAIEREEGQLQLCSRHRES (SEQ ID NO: 14) | HRES (SEQ ID NO: 28) | | |
| NMDAR1-3 | 11038636 | RRAIEREEGQLQLCSRHRES (SEQ ID NO: 14) | HRES (SEQ ID NO: 28) | | |
| NMDAR2C | 6006004 | TQGFPGPCTWRRISSLESEV (SEQ ID NO: 15) | ESEV (SEQ ID NO: 29) | X | AA180 |
| NMDAR3 | 560546 | FNGSSNGHVYEKLSSIESDV (SEQ ID NO: 11) | ESDV (SEQ ID NO: 12) | X | AA34.1 |
| NMDAR3A | 17530176 | AVSRKTELEEYQRTSRTCES (SEQ ID NO: 16) | TCES (SEQ ID NO: 30) | | |

TABLE 1-continued

NMDA Receptors With PL Sequences

| Name | GI or Acc# | C-terminal 20mer sequence | C-terminal 4mer sequence | PL? | internal PL ID |
|---|---|---|---|---|---|
| NMDAR2B | 4099612 | FNGSSNGHVYEKLSSIESDV (SEQ ID NO: 11) | ESDV (SEQ ID NO: 12) | X | |
| NMDAR2A | 558748 | LNSCSNRRVYKKMPSIESDV (SEQ ID NO: 17) | ESDV (SEQ ID NO: 12) | X | AA34.2 |
| NMDAR2D | 4504130 | GGDLGTRRGSAHFSSLESEV (SEQ ID NO: 18) | ESEV (SEQ ID NO: 29) | X | |
| Glutamate receptor delta 2 | AF009014 | QPTPTLGLNLGNDPDRGTSI (SEQ ID NO: 19) | GTSI (SEQ ID NO: 31) | X | |
| Glutamate receptor 1 | I28953 | MQSIPCMSHSSGMPLGATGL (SEQ ID NO: 20) | ATGL (SEQ ID NO: 32) | X | |
| Glutamate receptor 2 | L20814 | QNFATYKEGYNVYGIESVKI (SEQ ID NO: 21) | SVKI (SEQ ID NO: 33) | X | |
| Glutamate receptor 3 | AF167332 | QNYATYREGYNVYGTESVKI (SEQ ID NO: 22) | SVKI (SEQ ID NO: 33) | X | |
| Glutamate receptor 4 | U16129 | HTGTAIRQSSGLAVIASDLP (SEQ ID NO: 23) | SDLP (SEQ ID NO: 34) | X | |
| Glutamate receptor 5 | U16125 | SFTSILTCHQRRTQRKETVA (SEQ ID NO: 24) | ETVA (SEQ ID NO: 35) | X | |
| Glutamate receptor 6 | U16126 | EVINMHTFNDRRLPGKETMA (SEQ ID NO: 25) | ETMA (SEQ ID NO: 36) | X | |

Some peptides inhibit interactions between PSD-95 and multiple NMDAR subunits. In such instances, use of the peptide does not necessarily require an understanding of the respective contributions of the different NMDARs to excitatory neurotransmission. Other peptides are specific for a single NMDAR.

Peptides can include or be based on a PL motif from the C-terminus of any of the above subunits and have an amino acid sequence comprising [S/T]-X-[V/L]. This sequence preferably occurs at the C-terminus of the peptides of the invention. Preferred peptides have an amino acid sequence comprising [E/D/N/Q]-[S/T]-[D/E/Q/N]-[V/L] (SEQ ID NO:38) at their C-terminus. Exemplary peptides comprise: ESDV (SEQ ID NO:12), ESEV (SEQ ID NO:29), ETDV (SEQ ID NO:39), ETEV (SEQ ID NO:40), DTDV (SEQ ID NO:41), and DTEV (SEQ ID NO:42) as the C-terminal amino acids. Two particularly preferred peptides are KLSSIESDV (SEQ ID NO:5), and KLSSIETDV (SEQ ID NO:43). Such peptides usually have 3-25 amino acids (without an internalization peptide), peptide lengths of 5-10 amino acids, and particularly 9 amino acids (also without an internalization peptide) are preferred. In some such peptides, all amino acids are from the C-terminus of an NMDA receptor (not including amino acids from an internalization peptide).

Other peptides that inhibit interactions between PDS95 and NDMARs include peptides from PDZ domain 1 and/or 2 of PSD-95 or a subfragment of any of these that inhibits interactions between PSD-95 and an NMDA receptor, such as NR2B. Such active peptides comprise at least 50, 60, 70, 80 or 90 amino acids from PDZ domain 1 and/or PDZ domain 2 of PSD-95, which occur within approximately amino acids 65-248 of PSD-95 provided by Stathakism, Genomics 44(1):71-82 (1997) (human sequence) or NP_031890.1, GI:6681195 (mouse sequence) or corresponding regions of other species variants.

Peptides and peptidomimetics of the invention can contain modified amino acid residues for example, residues that are N-alkylated. N-terminal alkyl modifications can include e.g., N-Methyl, N-Ethyl, N-Propyl, N-Butyl, N-Cyclohexylmethyl, N-Cyclyhexylethyl, N-Benzyl, N-Phenylethyl, N-phenylpropyl. N-(3,4-Dichlorophenyl)propyl, N-(3,4-Difluorophenyl)propyl, and N-(Naphthalene-2-yl)ethyl).

Bach, J. Med. Chem. 51, 6450-6459 (2008) and WO 2010/004003 have described a series of analogs of NR2B9c (SEQ ID NO:6). PDZ-binding activity is exhibited by peptides having only three C-terminal amino acids (SDV). Bach also reports analogs having an amino acid sequence comprising or consisting of $X_1tSX_2V$ (SEQ ID NO:68), wherein t and S are alternative amino acids, $X_1$ is selected from among E, Q, and A, or an analogue thereof, $X_2$ is selected from among A, Q, D, N,N-Me-A, N-Me-Q, N-Me-D, and N-Me-N or an analog thereof. Optionally the peptide is N-alkylated in the P3 position (third amino acid from C-terminus, i.e. position occupied by tS). The peptide can be N-alkylated with a cyclohexane or aromatic substituent, and further comprises a spacer group between the substituent and the terminal amino group of the peptide or peptide analogue, wherein the spacer is an alkyl group, preferably selected from among methylene, ethylene, propylene and butylene. The aromatic substituent can be a naphthalen-2-yl moiety or an aromatic ring substituted with one or two halogen and/or alkyl group.

Other modifications can also be incorporated without adversely affecting the activity and these include substitution of one or more of the amino acids in the natural L-isomeric form with amino acids in the D-isomeric form. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form. Thus, a peptidomimetic may include 1, 2, 3, 4, 5, at least 50%, or all D-amino acid resides. A peptidomimetic containing some or all D residues is sometimes referred to an "inverso" peptide.

Peptidomimetics also include retro peptides. A retro peptide has a reverse amino acid sequence. Peptidomimetics also include retro inverso peptides in which the order of amino acids is reversed from so the originally C-terminal amino acid appears at the N-terminus and D-amino acids are used in place of L-amino acids. WO 2008/014917 describes a retro-inverso analog of Tat-NR2B9c having the amino acid sequence vdseisslk-rrqrrkkrgyin (SEQ ID NO:8) (lower case letters indicating D amino acids), and reports it to be effective inhibiting cerebral ischemia. Another effect peptide described herein is Rv-Tat-NR2B9c (RRRQRRK-KRGYKLSSIESDV; SEQ ID NO:70).

A linker, e.g., a polyethylene glycol linker, can be used to dimerize the active moiety of the peptide or the peptidomimetic to enhance its affinity and selectivity towards proteins containing tandem PDZ domains. See e.g., Bach et al., (2009) Angew. Chem. Int. Ed. 48:9685-9689 and WO 2010/004003. A PL motif-containing peptide is preferably dimerized via joining the N-termini of two such molecules, leaving the C-termini free. Bach further reports that a pentamer peptide IESDV (SEQ ID NO:71) from the C-terminus of NMDAR 2B was effective in inhibiting binding of NMDAR 2B to PSD-95. IETDV (SEQ ID NO:73) can also be used instead of IESDV. Optionally, about 2-10 copies of a PEG can be joined in tandem as a linker. Optionally, the linker can also be attached to an internalization peptide or lipidated to enhance cellular uptake. Examples of illustrative dimeric inhibitors are shown below (see Bach et al., PNAS 109 (2012) 3317-3322). Any of the PSD-95 inhibitors disclosed herein can be used instead of IETDV, and any internalization peptide or lipidating moiety can be used instead of tat. Other linkers to that shown can also be used.

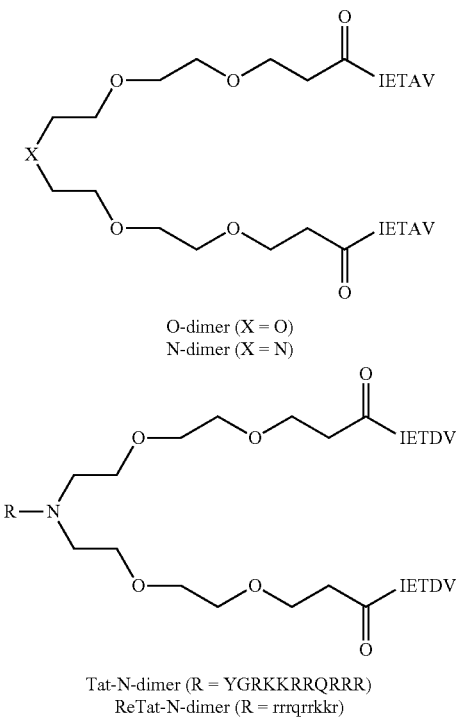

O-dimer (X = O)
N-dimer (X = N)

Tat-N-dimer (R = YGRKKRRQRRR)
ReTat-N-dimer (R = rrrqrrkkr)

IETAV is assigned SEQ ID NO:74, YGRKKRRQRRR SEQ ID NO:2, and rrrqrrkkr, SEQ NO:75, lower case letters indicated D-amino acids.

Appropriate pharmacological activity of peptides, peptidomimetics or other agent can be confirmed if desired, using previously described rat models of stroke before testing in the primate and clinical trials described in the present application. Peptides or peptidomimetics can also be screened for capacity to inhibit interactions between PSD-95 and NMDAR 2B using assays described in e.g., US 20050059597, which is incorporated by reference. Useful peptides typically have IC50 values of less than 50 µM, 25 µM, 10 µM, 0.1 µM or 0.01 µM in such an assay. Preferred peptides typically have an IC50 value of between 0.001-1 µM, and more preferably 0.001-0.05, 0.05-0.5 or 0.05 to 0.1 µM. When a peptide or other agent is characterized as inhibiting binding of one interaction, e.g., PSD-95 interaction to NMDAR2B, such description does not exclude that the peptide or agent also inhibits another interaction, for example, inhibition of PSD-95 binding to nNOS.

Peptides such as those just described can optionally be derivatized (e.g., acetylated, phosphorylated, myristoylated, geranylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Pharmacological agents also include small molecules that inhibit interactions between PSD-95 and NMDAR 2B, and/or other interactions described above. Suitable small-molecule inhibitors are described in, e.g., WO/2009/006611. An exemplary class of suitable compounds are of the formula:

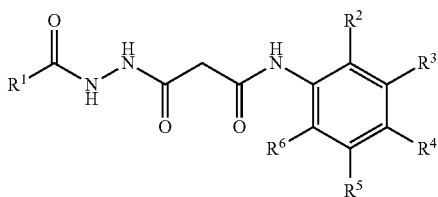

wherein $R^1$ is a member selected from the group consisting of cyclohexyl substituted with 0-4 $R^7$, phenyl substituted with 0-4 $R^7$, —$(CH_2)_n$—$(CHR^8R^9)$, a branched $C_{1-6}$ alkyl (isopropyl, isobutyl, 1-isopropyl-2-methyl-butyl, 1 ethyl-propyl), and —NH—C(O)—$(CR^{10}R^{11})_v$H;

each $R^7$ is independently a member selected from the group consisting of $C_{1-6}$ alkyl, $C_{1-6}$ alkoxy, —C(O)$R^{12}$, OH, COOH, —NO, N-substituted indoline and a cell membrane translocation peptide;

each $R^8$ and $R^9$ is independently selected from the group consisting of H, OH, cyclohexane, cyclopentane, phenyl, substituted phenyl and cyclopentadiene;

each $R^{10}$ and $R^{11}$ is independently selected from the group consisting of H, cyclohexane, phenyl and a cell membrane translocation peptide;

$R^{12}$ is a member selected from the group consisting of $C_{1-6}$ alkyl and aryl; and each of u and v are independently from 0 to 20;

wherein one of $R^2$, $R^3$, $R^4$, $R^5$ and $R^6$ is —COOH, and wherein the remainder of $R^2$, $R^3$, $R^4$, $R^5$ and $R^6$ are each independently selected from the group consisting of F, H, $OCH_3$ and $CH_3$.

One such compound is 0620-0057, the structure of which is:

0620-0057

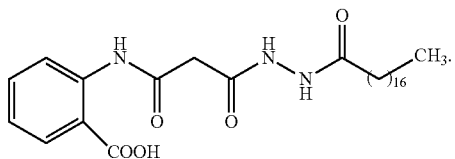

A pharmacological agent can be linked to an internalization peptide to facilitate uptake into cells and/or across the blood brain barrier. Internalization peptides are a well-known class of relatively short peptides that allow many cellular or viral proteins to traverse membranes. Internalization peptides, also known as cell membrane transduction peptides or cell penetrating peptides can have e.g., 5-30 amino acids. Such peptides typically have a cationic charge from an above normal representation (relative to proteins in general) of arginine and/or lysine residues that is believed to facilitate their passage across membranes. Some such peptides have at least 5, 6, 7 or 8 arginine and/or lysine residues. Examples include the antennapedia protein (Bonfanti, Cancer Res. 57, 1442-6 (1997)) (and variants thereof), the tat protein of human immunodeficiency virus, the protein VP22, the product of the UL49 gene of herpes simplex virus type 1, Penetratin, SynB1 and 3, Transportan, Amphipathic, gp41NLS, polyArg, and several plant and bacterial protein toxins, such as ricin, abrin, modecein, diphtheria toxin, cholera toxin, anthrax toxin, heat labile toxins, and Pseudomonas aeruginosa exotoxin A (ETA). Other examples are described in the following references (Temsamani, Drug Discovery Today, 9(23):1012-1019, 2004; De Coupade, Biochem J., 390:407-418, 2005; Saalik Bioconjugate Chem. 15: 1246-1253, 2004; Zhao, Medicinal Research Reviews 24(1):1-12, 2004; Deshayes, Cellular and Molecular Life Sciences 62:1839-49, 2005); Gao, ACS Chem. Biol. 2011, 6, 484-491, SG3 (RLSGMNEVLS-FRWL) (SEQ ID NO:77) (all incorporated by reference).

A preferred internalization peptide is tat from the HIV virus. A tat peptide reported in previous work comprises or consists of the standard amino acid sequence YGRK-KRRQRRR (SEQ ID NO:2) found in HIV Tat protein. If additional residues flanking such a tat motif are present (beside the pharmacological agent) the residues can be for example natural amino acids flanking this segment from a tat protein, spacer or linker amino acids of a kind typically used to join two peptide domains, e.g., gly (ser)$_4$ (SEQ ID NO:44), TGEKP (SEQ ID NO:45), GGRRGGGS (SEQ ID NO:46), or LRQRDGERP (SEQ ID NO:47) (see, e.g., Tang et al. (1996), J. Biol. Chem. 271, 15682-15686; Hennecke et al. (1998), Protein Eng. 11, 405-410)), or can be any other amino acids that do not significantly reduce capacity to confer uptake of the variant without the flanking residues. Preferably, the number of flanking amino acids other than an active peptide does not exceed ten on either side of YGRK-KRRQRRR (SEQ ID NO:2). One suitable tat peptide comprising additional amino acid residues flanking the C-terminus of YGRKKRRQRRR (SEQ ID NO:2) is YGRKKRRQRRRPQ (SEQ ID NO:48). However, preferably, no flanking amino acids are present. Other tat peptides that can be used include GRKKRRQRRRPQ (SEQ ID NO:4) and GRKKRRQRRRP (SEQ ID NO:72).

Variants of the above tat peptide having reduced capacity to bind to N-type calcium channels are described by WO/2008/109010. Such variants can comprise or consist of an amino acid sequence XGRKKRRQRRR (SEQ ID NO:49), in which X is an amino acid other than Y or nothing (in which case G is a free N-terminal residue). A preferred tat peptide has the N-terminal Y residue substituted with F. Thus, a tat peptide comprising or consisting of FGRK-KRRQRRR (SEQ ID NO:3) is preferred. Another preferred variant tat peptide consists of GRKKRRQRRR (SEQ ID NO:1). Another preferred tat peptide comprises or consists of RRRQRRKKRG (SEQ ID NO:10) or RRRQRRKKRGY (SEQ ID NO:26) (amino acids 1-10 or 1-11 of SEQ ID NO:70). Other tat derived peptides that facilitate uptake of a pharmacological agent without inhibiting N-type calcium channels include those presented in Table 2 below.

TABLE 2

| | | |
|---|---|---|
| X - FGRKKRRQRRR (F-Tat) | (SEQ ID NO: 69) |
| X - GKKKKKQKKK | (SEQ ID NO: 50) |
| X - RKKRRQRRR | (SEQ ID NO: 51) |
| X - GAKKRRQRRR | (SEQ ID NO: 52) |
| X - AKKRRQRRR | (SEQ ID NO: 53) |
| X - GRKARRQRRR | (SEQ ID NO: 54) |
| X - RKARRQRRR | (SEQ ID NO: 55) |
| X - GRKKARQRRR | (SEQ ID NO: 56) |
| X - RKKARQRRR | (SEQ ID NO: 57) |
| X - GRKKRRQARR | (SEQ ID NO: 58) |

TABLE 2-continued

| | | |
|---|---|---|
| X - RKKRRQARR | (SEQ ID NO: 59) | |
| X - GRKKRRQRAR | (SEQ ID NO: 60) | |
| X - RKKRRQRAR | (SEQ ID NO: 61) | |
| X - RRPRPRRPRR | (SEQ ID NO: 62) | |
| X - RRARRARRARR | (SEQ ID NO: 63) | |
| X - RRRARRRARR | (SEQ ID NO: 64) | |
| X - RRRPRRRPRR | (SEQ ID NO: 65) | |
| X - RRPRRPRR | (SEQ ID NO: 66) | |
| X - RRARRARR | (SEQ ID NO: 67) | |

X can represent a free amino terminus, one or more amino acids, or a conjugated moiety. Internalization peptides can be used in inverso or retro or inverso retro form with or without the linked peptide or peptidomimetic being in such form. For example, a preferred chimeric peptide has an amino acid sequence comprising or consisting of RRRQR-RKKRGY-KLSSIESDV (SEQ ID NO:70, also known as NA-1 or Tat-NR2B9c) or having an amino acid sequence comprising or consisting of RRRQRRKKRGY-KLSSI-ETDV (SEQ ID NO:37).

Internalization peptides can be attached to pharmacological agents by conventional methods. For example, the agents can be joined to internalization peptides by chemical linkage, for instance via a coupling or conjugating agent. Numerous such agents are commercially available and are reviewed by S. S. Wong, Chemistry of Protein Conjugation and Cross-Linking, CRC Press (1991). Some examples of cross-linking reagents include J-succinimidyl 3-(2-pyridyldithio) propionate (SPDP) or N,N'-(1,3-phenylene)bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

For pharmacological agents that are peptides attachment to an internalization peptide can be achieved by generating a fusion protein comprising the peptide sequence fused, preferably at its N-terminus, to an internalization peptide.

Instead of or as well as linking a peptide (or other agent) inhibiting PSD-95 to an internalization peptide, such a peptide can be linked to a lipid (lipidation) to increase hydrophobicity of the conjugate relative to the peptide alone and thereby facilitate passage of the linked peptide across cell membranes and/or across the brain barrier. Lipidation is preferably performed on the N-terminal amino acid but can also be performed on internal amino acids, provided the ability of the peptide to inhibit interaction between PSD-95 and NMDAR 2B is not reduced by more than 50%. Preferably, lipidation is performed on an amino acid other than one of the four most C-terminal amino acids. Lipids are organic molecules more soluble in ether than water and include fatty acids, glycerides and sterols. Suitable forms of lipidation include myristoylation, palmitoylation or attachment of other fatty acids preferably with a chain length of 10-20 carbons, such as lauric acid and stearic acid, as well as geranylation, geranylgeranylation, and isoprenylation. Lipidations of a type occurring in posttranslational modification of natural proteins are preferred. Lipidation with a fatty acid via formation of an amide bond to the alpha-amino group of the N-terminal amino acid of the peptide is also preferred. Lipidation can be by peptide synthesis including a prelipidated amino acid, be performed enzymatically in vitro or by recombinant expression, by chemical crosslinking or chemical derivatization of the peptide. Amino acids modified by myristoylation and other lipid modifications are commercially available.

Lipidation preferably facilitates passage of a linked peptide (e.g., KLSSIESDV (SEQ ID NO:5), or KLSSIETDV (SEQ ID NO:43)) across a cell membrane and/or the blood brain barrier without causing a transient reduction of blood pressure as has been found when a standard tat peptide is administered at high dosage (e.g., at or greater than 3 mg/kg), or at least with smaller reduction that than the same peptide linked to a standard tat peptide.

Pharmacologic peptides, optionally fused to tat peptides, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

III. Agents and Methods for Reperfusion

Plaques and blood clots (also known as emboli) causing ischemia can be dissolved, removed or bypassed by both pharmacological and physical means. The dissolving, removal of plaques and blood clots and consequent restoration of blood flow is referred to as reperfusion. One class of agents acts by thrombolysis. These agents work by stimulating fibrinolysis by plasmin through infusion of tissue plasminogen activators (tPA). Plasmin clears cross-linked fibrin mesh (the backbone of a clot), making the clot soluble and subject to further proteolysis by other enzymes, and restores blood flow in occluded blood vessels. Examples of thrombolytic agents include tissue plasminogen activator t-PA, alteplase (Activase), reteplase (Retavase), tenecteplase (TNKase), anistreplase (Eminase), streptokinase (Kabikinase, Streptase), and urokinase (Abbokinase).

Another class of drugs that can be used for reperfusion is vasodilators. These drugs act by relaxing and opening up blood vessels thus allowing blood to flow around an obstruction. Some examples of types of vasodilators alpha-adrenoceptor antagonists (alpha-blockers), Angiotensin receptor blockers (ARBs), Beta$_2$-adrenoceptor agonists ($\beta_2$-agonists), calcium-channel blockers (CCBs), centrally acting sympatholytics, direct acting vasodilators, endothelin receptor antagonists, ganglionic blockers, nitrodilators, phosphodiesterase inhibitors, potassium-channel openers, and renin inhibitors.

Another class of drugs that can be used for reperfusion is hypertensive drugs (i.e., drugs raising blood pressure), such as epinephrine, phenylephrine, pseudoephedrine, norepinephrine; norephedrine; terbutaline; salbutamol; and methylephedrine. Increased perfusion pressure can increase flow of blood around an obstruction.

Mechanical methods of reperfusion include angioplasty, catheterization, and artery bypass graft surgery, stenting, embolectomy, or endarterectomy. Such procedures restore plaque flow by mechanical removal of a plaque, holding a blood vessel open, so blood can flow around a plaque or bypassing a plaque.

Other mechanical methods of reperfusion include use of a device that diverts blood flow from other areas of the body to the brain. An example is a catheter partially occluding the aorta, such as the CoAxia NeuroFlo™ catheter device, which has recently been subjected to a randomized trial and may get FDA approval for stroke treatment. This device has been used on subjects presenting with stroke up to 14 hours after onset of ischemia.

Use of a non-thrombolytic agent or mechanical method of reperfusion does not subject a peptide PSD-95 inhibitor to proteolytic cleavage and therefore, which may be an advantage if the PSD-95 inhibitor and reperfusion are administered simultaneously or proximate in time.

IV. Stroke

A stroke is a condition resulting from impaired blood flow in the CNS regardless of cause. Potential causes include embolism, hemorrhage and thrombosis. Some neuronal cells die immediately as a result of impaired blood flow. These cells release their component molecules including glutamate, which in turn activates NMDA receptors, which raise intracellular calcium levels, and intracellular enzyme levels leading to further neuronal cell death (the excitotoxicity cascade). The death of CNS tissue is referred to as infarction. Infarction Volume (i.e., the volume of dead neuronal cells resulting from stroke in the brain) can be used as an indicator of the extent of pathological damage resulting from stroke. The symptomatic effect depends both on the volume of an infarction and where in the brain it is located. Disability index can be used as a measure of symptomatic damage, such as the Rankin Stroke Outcome Scale (Rankin, Scott Med J; 2:200-15 (1957)) and the Barthel Index. The Rankin Scale is based on assessing directly the global conditions of a subject as follows.

TABLE 3

0 No symptoms at all
1 No significant disability despite symptoms; able to carry out all usual duties and activities.
2 Slight disability; unable to carry out all previous activities but able to look after own affairs without assistance.
3 Moderate disability requiring some help, but able to walk without assistance
4 Moderate to severe disability; unable to walk without assistance and unable to attend to own bodily needs without assistance.
5 Severe disability; bedridden, incontinent, and requiring constant nursing care and attention.

The Barthel Index is based on a series of questions about the subject's ability to carry out 10 basic activities of daily living resulting in a score between 0 and 100, a lower score indicating more disability (Mahoney et al., Maryland State Medical Journal 14:56-61 (1965)).

Alternatively stroke severity/outcomes can be measured using the NIH stroke scale, available at world wide web ninds.nih.gov/doctors/NIH_Stroke_Scale_Booklet.pdf.

The scale is based on the ability of a subject to carry out 11 groups of functions that include assessments of the subject's level of consciousness, motor, sensory and language functions.

An ischemic stroke refers more specifically to a type of stroke that is caused by blockage of blood flow to the brain. The underlying condition for this type of blockage is most commonly the development of fatty deposits lining the vessel walls. This condition is called atherosclerosis. These fatty deposits can cause two types of obstruction. Cerebral thrombosis refers to a thrombus (blood clot) that develops at the clogged part of the vessel "Cerebral embolism" refers generally to a blood clot or atheroma that forms at another location in the circulatory system, usually the heart and large arteries of the upper chest and neck. A portion of the blood clot and/or atheroma then breaks loose, enters the bloodstream and travels through the brain's blood vessels until it reaches vessels too small to let it pass. A second important cause of embolism is an irregular heartbeat, known as arterial fibrillation. It creates conditions in which clots can form in the heart, dislodge and travel to the brain. Additional potential causes of ischemic stroke are hemorrhage, thrombosis, dissection of an artery or vein, a cardiac arrest, shock of any cause including hemorrhage, and iatrogenic causes such as direct surgical injury to brain blood vessels or vessels leading to the brain or cardiac surgery. Ischemic stroke accounts for about 83 percent of all cases of stroke.

Transient ischemic attacks (TIAs) are minor or warning strokes. In a TIA, conditions indicative of an ischemic stroke are present and the typical stroke warning signs develop. However, the obstruction (blood clot) occurs for a short time and tends to resolve itself through normal mechanisms. Subjects undergoing heart surgery are at particular risk of transient cerebral ischemic attack.

Hemorrhagic stroke accounts for about 17 percent of stroke cases. It results from a weakened vessel that ruptures and bleeds into the surrounding brain. The blood accumulates and compresses the surrounding brain tissue. The two general types of hemorrhagic strokes are intracerebral hemorrhage and subarachnoid hemorrhage. Hemorrhagic stroke result from rupture of a weakened blood vessel ruptures. Potential causes of rupture from a weakened blood vessel include a hypertensive hemorrhage, in which high blood pressure causes a rupture of a blood vessel, or another underlying cause of weakened blood vessels such as a ruptured brain vascular malformation including a brain aneurysm, arteriovenous malformation (AVM) or cavernous malformation. Hemorrhagic strokes can also arise from a hemorrhagic transformation of an ischemic stroke which weakens the blood vessels in the infarct, or a hemorrhage from primary or metastatic tumors in the CNS which contain abnormally weak blood vessels. Hemorrhagic stroke can also arise from iatrogenic causes such as direct surgical injury to a brain blood vessel. An aneurysm is a ballooning of a weakened region of a blood vessel. If left untreated, the aneurysm may continue to weaken until it ruptures and bleeds into the brain. An arteriovenous malformation (AVM) is a cluster of abnormally formed blood vessels. A cavernous malformation is a venous abnormality that can cause a hemorrhage from weakened venous structures. Any one of these vessels can rupture, also causing bleeding into the brain. Hemorrhagic stroke can also result from physical trauma. Hemorrhagic stroke in one part of the brain can lead to ischemic stroke in another through shortage of blood lost in the hemorrhagic stroke.

V. Subjects Amenable to Treatment

Subjects amenable to treatment include subjects presenting with signs(s) and/or symptom(s) of ischemia either in the CNS or elsewhere in the body but affecting a blood vessel whose obstruction may impede blood flow through the brain. These subjects include subjects presenting with sign(s) and/or symptoms of stroke, myocardial ischemia, pulmonary embolism, limb ischemia, renal or retinal ischemia. Such subjects include subjects in which such a condition is suspected but other conditions cannot be excluded, as well as subjects who have been diagnosed according to generally recognized criteria, e.g., DSM IV TR.

Subjects amenable to treatment also include subjects at risk of ischemia but in which onset of ischemia has not yet occurred. A subject is at risk if he or she has a higher risk of developing ischemia than a control population. The control population may include one or more individuals selected at random from the general population (e.g., matched by age, gender, race and/or ethnicity) who have not been diagnosed or have a family history of the disorder. A subject can be considered at risk for a disorder if a "risk factor" associated with that disorder is found to be associated with that subject. A risk factor can include any activity, trait, event or property associated with a given disorder, for example, through statistical or epidemiological studies on a population of subjects. A subject can thus be classified as being at risk for a disorder even if studies identifying the underlying risk factors did not include the subject specifically. For example, a subject undergoing heart surgery is at risk of transient cerebral ischemic attack because the frequency of transient cerebral ischemic attack is increased in a population of subjects who have undergone heart surgery as compared to a population of subjects who have not.

Subjects at risk of ischemia affecting the brain include those undergoing a surgical procedure on the brain or CNS, such as endovascular surgery, clipping, stenting or microcathetherization. Such subjects also include those undergoing surgery elsewhere in the body that affects a blood vessel supplying the brain (that is connecting the brain to the heart, for example, carotid arteries and jugular veins) or on an artery supplying blood to the retina, kidney, spinal cord or limbs. A preferred class of subjects are those undergoing endovascular surgery to treat a brain aneurysm. Subjects undergoing these types of surgery are at enhanced risk of ischemia affects the CNS. Subjects at risk of stroke also include patients who are smokers, hypertensive, diabetic, hyper-cholesterolemic. Subjects especially at a high risk are those who have had a prior stroke, minor stroke, or transient ischemic attack.

VI. Combined Methods of Treatment

The combined methods involved administering a PSD-95 inhibitor and a form of reperfusion therapy to a subject amenable to treatment. The PSD-95 inhibitor and reperfusion can be administered in either order or at the same time. Usually, the PSD-95 inhibitor and reperfusion are administered at the same, overlapping or proximate times (i.e., within a 15 minutes interval) or the PSD-95 inhibitor is administered first.

For treatment of ischemias that cannot be predicted in advance, the PSD-95 inhibitor can be administered as soon as possible or practical after onset of ischemia. For example, the PSD-95 inhibitor can be administered within a period of 0.5, 1, 2, 3, 4, 5, 6, 9, 12 or 24 hours after the onset of ischemia. For ischemias that can be predicted in advance, the PSD-95 inhibitor can be administered before, concurrent with or after onset of ischemia. For example, for an ischemia resulting from surgery, the PDS95 inhibitor is sometimes routinely administered in a period starting 30 minutes before beginning surgery and ending 1, 2, 3, 4, 5, 6, 9, 12 or 24 hours after surgery without regard to whether ischemia has or will develop. Because the PSD-95 inhibitor is free of serious side effects, it can be administered when stroke or other ischemic conditions are suspected without a diagnosis according to art-recognized criteria having been made. For example, the PSD-95 inhibitor can be administered at the location where the stroke has occurred (e.g., in the patients' home) or in an ambulance transporting a subject to a hospital. The PSD-95 inhibitor can also be safely administered to a subject at risk of stroke or other ischemic conditions before onset who may or may not actually develop the condition.

Following, or sometimes before, administration of the PSD-95 inhibitor, a subject presenting with sign(s) and/or symptom(s) of ischemia can be subject to further diagnostic assessment to determine whether the subject has ischemia within or otherwise affecting the CNS and determine whether the subject has or is susceptible to hemorrhage. Most particularly in subjects presenting with symptoms of stroke, testing attempts to distinguish whether the stroke is the result of hemorrhage or ischemia, hemorrhage accounting for about 17% of strokes. Diagnostic tests can include a scan of one or more organs, such as a CAT scan, MRI or PET imaging scan or a blood test for a biomarker that suggests that a stroke has occurred. Several biomarkers associated with stroke are known including B-type neurotrophic growth factor, von Willebrand factor, matrix metalloproteinase-9, and monocyte chemotactic protein-1 (see Reynolds et al., *Clinical Chemistry* 49: 1733-1739 (2003)). The organ(s) scanned include any suspected as being the site of ischemia (e.g., brain, heart, limbs, spine, lungs, kidney, retina) as well as any otherwise suspect of being the source of a hemorrhage. A scan of the brain is the usual procedure for distinguishing between ischemic and hemorrhagic stroke. Diagnostic assessment can also include taking or reviewing a subject's medical history and performing other tests. Presence of any of the following factors alone or in combination can be used in assessing whether reperfusion therapy presents an unacceptable risk: subject's symptoms are minor or rapidly improving, subject had seizure at onset of stroke, subject has had another stroke or serious head trauma within the past 3 months, subject had major surgery within the last 14 days, subject has known history of intracranial hemorrhage, subject has sustained systolic blood pressure >185 mmHg, subject has sustained diastolic blood pressure >110 mmHg, aggressive treatment is necessary to lower the subject's blood pressure, subject has symptoms suggestive of subarachnoid hemorrhage, subject has had gastrointestinal or urinary tract hemorrhage within the last 21 days, subject has had arterial puncture at noncompressible site within the last 7 days, subject has received heparin with the last 48 hours and has elevated PTT, subject's prothrombin time (PT) is >15 seconds, subject's platelet count is <100,000 µL. subject's serum glucose is <50 mg/dL or >400 mg/dL, subject is a hemophiliac or has other clotting deficiencies.

The further diagnostic investigation determines according to recognized criteria or at least with greater probability that before the investigation whether the subject has an ischemic condition, and whether the subject has a hemorrhage, has an unacceptable risk of hemorrhage or is otherwise excluded from receiving reperfusion therapy due to unacceptable risk of side effects. Subjects in which a diagnosis of an ischemic condition within or otherwise likely to affect the CNS is confirmed who are without unacceptable risk of side effects can then be subject to reperfusion therapy. Preferably, reperfusion therapy is performed as soon as practical after completion of any diagnostic procedures. In some subjects, reperfusion therapy is commenced more than 0, 1, 2, 3, 4, 4.5, 5, 6, 7, 8, 10, 12, 15, 18, or 24 hr after onset of ischemia. In strokes occurring in a medical setting (e.g., during endovascular procedures) treatment can begin less than 1 hour after onset. In some subjects, reperfusion therapy is commenced 0.5-6, 0.5-12, 0.5-18 or 0.5-24 hr after onset of ischemia. In some subjects, reperfusion therapy is commenced outside the usual 3-4.5 hr window in which reperfusion therapy has hitherto been considered to effective. For example in some subjects, reperfusion therapy is commenced more than 3 hours or more than 4.5 hours after onset of ischemia and up to 24 or 48 hours after onset of ischemia. In some subjects, reperfusion therapy is commenced, after 5, 6, 7, 8, 9 or 10 hours and up to 24 or 48 hours after onset of ischemia. In some subjects, reperfusion therapy is commenced from 275-390 minutes after onset of ischemia. In some subjects, reperfusion therapy is commenced irrespective of the time of onset of ischemia provided that they qualify for reperfusion based on specific diagnostic criteria such as the absence of a completed infarct on a CT scan, evidence of an ischemic penumbra by computerized tomography (CT), magnetic resonance imaging (MRI) or positron emission tomography (PET) imaging criteria, and the absence of a brain hemorrhage.

The time of reperfusion can also be measured from the administration of the PSD-95 inhibitor. The interval can be, for example, 5 minutes to 24 or 48 hours (the interval between PSD-95 administration and reperfusion, here as elsewhere in this application, being measured from initiating PSD-95 inhibitor administration to initiating reperfusion administration). The interval may be for example, 15 min to 6 hr, 15 min to 4.5 hr, 15 min to 3 hr, 15 min to 1 hr, 30 minutes to 6 hours, or 30 min to 3 hours, or 30 min to 4.5 hours, or 1-3 hours, or 1-4.5 hours. A longer interval can be advantageous for peptide PSD-95 inhibitors, such as Tat-NR2B9c, used in combination with agents for reperfusion acting via proteolysis (e.g., tPA), because it gives the inhibitor a longer period to exert its effect before it is subject to proteolytic degradation by plasmin resulting.

Subjects in which an ischemic condition is not confirmed or is considered unlikely are not usually administered reperfusion therapy. Such subjects may not have received any benefit from the PSD-95 inhibitor but are also not worse off than not having been treated. Subjects in which an ischemic condition is confirmed or considered likely but are considered at unacceptable risk of side effects from reperfusion therapy are not administered reperfusion therapy. Such subjects may have obtained benefit of the PSD-95 inhibitor but are spared the risk of unacceptable side effects from reperfusion therapy.

Both treatment with a PSD-95 inhibitor and reperfusion therapy independently have ability to reduce infarction size and functional deficits due to ischemia. When used in combination according to the present methods, the reduction in infarction size and/or functional deficits is preferably greater than that front use of either agent alone administered under a comparable regime other than for the combination (i.e., co-operative). More preferably, the reduction in infarction side and/or functional deficits is at least additive or preferably more than additive (i.e., synergistic) of reductions achieved by the agents alone under a comparable regime except for the combination. In some regimes, the reperfusion therapy is effective in reducing infarction size and/or functional times at a time post onset of ischemia (e.g., more than 4.5 hr) when it would be ineffective but for the concurrent or prior administration of the PSD-95 inhibitor. Put another way, when a subject is administered a PSD-95 inhibitor and reperfusion therapy, the reperfusion therapy is preferably at least as effective as it would be if administered at an earlier time without the PSD-95 inhibitor. Thus, the PSD-95 inhibitor effectively increases the efficacy of the reperfusion therapy by reducing one or more damaging effects of ischemia before or as reperfusion therapy takes effects. The PSD-95 inhibitor can thus compensate for delay in administering the reperfusion therapy whether the delay be from delay in the subject recognizing the danger of his or her initial symptoms delays in transporting a subject to a hospital or other medical institution or delays in performing diagnostic procedures to establish presence of ischemia and/or absence of hemorrhage or unacceptable risk thereof. Statistically significant combined effects of PSD-95 inhibitor and reperfusion therapy including additive or synergistic effects can be demonstrated between populations in a clinical trial or between populations of animal models in pre-clinical work.

VI. Effective Regimes of Administration

A PSD-95 inhibitor is administered in an amount, frequency and route of administration effective to reduce, inhibit or delay one or more damaging effects of ischemia on the CNS. Unless otherwise indicated, dosages for inhibitors that are chimeric agents including a pharmacologic agent linked to an internalization peptide refer to the whole agent rather than just the pharmacological agent component of the chimeric agent. An effective amount means an amount of agent sufficient significantly to reduce, inhibit or delay one or more damaging effects of ischemia in a population of subjects (or animal models) suffering from the disease treated with an agent of the invention relative to the damage in a control population of subjects (or animal models) suffering from that disease or condition who are not treated with the agent. The amount is also considered effective if an individual treated subject achieves an outcome more favorable than the mean outcome in a control population of comparable subjects not treated by methods of the invention. An effective regime involves the administration of an effective dose at a frequency and route of administration needed to achieve the intended purpose.

When the condition requiring treatment is stroke, the outcome can be determined by infarction volume or disability index, and a dosage can be recognized as effective if an individual treated subject shows a disability of two or less on the Rankin scale and 75 or more on the Barthel scale, see Lees et at l., N Engl J Med 2006; 354:588-600 or if a population of treated subjects shows a significantly improved (i.e., less disability) distribution of scores on any disability scale (e.g., Barthel, Rankin, NIH Stroke Scale) than a comparable untreated population, or if a population of treated subjects shows significantly reduced infarction size or number compared with a comparable untreated population. A single dose of agent is usually sufficient for treatment of stroke. However, multiple dosages can be administered at intervals of e.g., 1, 2, 3, 6, 12, 18, or 24 hours until presence of a completed infarct is detected on a CT scan or until no further benefit is seen.

Depending on the agent, administration can be parenteral, intravenous, nasal, oral, subcutaneous, intra-arterial, intracranial, intrathecal, intraperitoneal, topical, intranasal or intramuscular. Intravenous administration is preferred for peptide agents.

For chimeric agents including an internalization peptide, particularly a HIV tat peptide comprising the amino acid sequence YGRKKRRQRRR (SEQ ID NO:2), administration of the agent may or may not be combined with an anti-inflammatory agent to reduce release of histamine and its downstream effects associated with high levels of the internalization peptide. Preferred agents for co-administration are inhibitors of mast cell degranulation, such as cromolyn or lodoxamide or any others listed herein. Antihistamines or corticosteroids can also be used, particularly in combinations or higher dosages (see WO2009/076105 and WO2010/144742).

For administration to humans, a preferred dose of the chimeric agent Tat-NR2B9c is 2-3 mg/kg and more preferably 2.6 mg/kg. Indicated dosages should be understood as including the margin of error inherent in the accuracy with which dosages can be measured in a typical hospital setting. The dose is preferred because it is the maximum dose with which the agent can be administered without release of significant amounts of histamine and the ensuing sequelae in most subjects. Although release of histamine at higher dosages can be controlled by co-administration of an anti-inflammatory as discussed above and in any event usually spontaneously resolves without adverse events, it can best be avoided by keeping the dose below 3 mg/kg and preferably at 2-3 mg/kg, more preferably 2.6 mg/kg. Such amounts are for single dose administration, i.e., one dose per episode of disease. Such doses can also be administered daily, or more frequently. Lower doses may be used, optionally 1-2 mg/kg, or 0.5-1 mg/kg, 0.1-0.5 mg/kg or less than 0.1 mg/kg. For repeated dose regimes, even lower dosages may be used.

The dosages indicated above are for the chimeric agent Tat-NR2B9c (YGRKKRRQRRRKLSSIESDV; SEQ ID NO:6). Equivalent dosages for other agents to achieve the same effect can be determined by several approaches. For close variants of that agent in which one or a few amino acids are substituted, inserted or deleted and the molecular weight remains the same within about +/−25%, the above dosages are still a good guide. However, in general, for other agents, equivalent dosages can vary depending on the molecular weight of the agent with and without internalization peptide if present, its Kd for its target, and its pharmacokinetic and pharmacodynamic parameters. For some agents, equivalent dosages can be calculated so as to deliver an equimolar amount of the pharmacological agent. For other agent, further adjustment can be made to account for differences in Kd or pharmacokinetic or pharmacodynamic parameters. For some agents, equivalent dosages are determined empirically from the dose achieved to reach the same endpoint in an animal model or a clinical trial.

Peptide agents, such as Tat-NR2B9c are preferably delivered by infusion into a blood vessel, more preferably by intravenous infusion. For the chimeric agent Tat-NR2B9c, a preferred infusion time providing a balance between these considerations is 5-15 minutes and more preferably 10 minutes. Indicated times should be understood as including a marking of error of +/−10%. Infusion times do not include any extra time for a wash out diffusion to wash out any remaining droplets from an initial diffusion that has otherwise proceeded to completion. The infusion times for Tat-NR2B9c can also serve as a guide for other pharmacological agents, optionally linked to internalization peptides, particularly close variants of Tat-NR2B9c, as discussed above.

The PSD-95 inhibitor can be administered in the form of a pharmaceutical composition. Pharmaceutical compositions are typically manufactured under GMP conditions. Pharmaceutical compositions for parenteral administration are preferentially sterile (e.g., filter sterilization of peptide) and free of pyrogens. Pharmaceutical compositions can be provided in unit dosage form (i.e., the dosage for a single administration). Pharmaceutical compositions can be formulated in conventional manner using one or more physiologically acceptable carriers, diluents, excipients or auxiliaries that facilitate processing of chimeric agents into preparations which can be used pharmaceutically. Proper formulation is dependent on the route of administration chosen.

An exemplary formulation of the chimeric agent Tat-NR2B9c contains the peptide in normal saline (0.8-1.0% and preferably 0.9% saline) or phosphate buffered saline at a concentration of 10-30 mg/ml, for example 16-20 or 18 mg/ml or 20 mg/ml. When stored frozen, such a composition is stable (insignificant degradation or aggregation of the peptide) for a period of four or more years. Although additional excipients can be added, normal saline or phosphate buffered saline without such excipients is sufficient to obtain this stability. For use such a composition is thawed and diluted into a larger volume of normal saline for infusion into a blood vessel.

Many examples of pharmacological agent for reperfusion are in clinical use. Such agents can be used in the present combination methods in accordance with their conventional formulations, doses, routes of administration, and frequency of administration (see Physician's Desk Reference and applicable package inserts). For example, tPA or other thrombolytic agents can be administered intravenously at a dose of e.g., 0.5-1.5 mg/kg, preferably 0.9 mg/kg in humans. tPA and other thrombolytic agents can also be given intra-arterially preferably at a dose of 0.02-0.1 mg/kg/hour in human patients for up to 36 hours. tPA and other thrombolytic agents can also be administered directly to a site of impaired blood flow, e.g., an emboli in the brain, for which the preferred dose is 2 mg in human patients (or less in patient with weight less than 30 kg). Localized administration is preferably via a catheter. Direct administration to the site of infarction reduces potential exposure of peptide PSD-95 inhibitors to proteolytic degradation. Likewise, mechanical methods of reperfusion can be employed in accordance with conventional practice.

EXAMPLES

Example 1: Neuroprotection after Stroke in Gyrencephalic Old World Primates

Introduction

We used higher order gyrencephalic nonhuman primates (NHPs) which bear genetic, anatomic and behavioral similarities to humans and tested neuroprotection by PSD95 inhibitors, compounds that uncouple postsynaptic density protein PSD-95 from neurotoxic signaling pathways. Here we show that stroke damage can be prevented in NHPs in which a PSD95 inhibitor is administered after stroke onset. This treatment reduced infarct volumes as gauged by magnetic resonance imaging (MRI) and histology, preserved the capacity of ischemic cells to maintain gene transcription in genome-wide screens of ischemic brain tissue, and significantly preserved neurological function in neurobehavioral assays. The degree of tissue neuroprotection by MRI corresponded strongly to the preservation of neurological function, supporting the unproven dictum that brain tissue integrity can reflect functional outcome. Our findings establish that tissue neuroprotection and improved functional outcome after stroke is unequivocally achievable in gyrencephalic NHPs using PSD95 inhibitors.

General Experimental Flow and Assessments

We conducted all experiments with allocation concealment and blinded assessment of all outcomes. The primary outcome measure was infarct volume at 30 days measured from a T2-weighted MRI study. Anatomical secondary outcomes were infarct volumes at 4 h and 24 h by diffusion-weighted imaging (DWI) MRI, at 24 h by T2 MRI and at 30d by T2 MRI and histology. Neurobehavioral outcomes were measured throughout the 30d observation period using the non-human primate stroke scale (NHPSS) and a sensorimotor battery of tasks comprising the hill and valley task, two-tube task and six well task. A scheme for the treatments and assessments is presented in FIG. 1A, and a description follows below. The times of middle cerebral artery occlusion varied between experiments as described below.

Macaques were randomized to receive a 10 min intravenous infusion of Tat-NR2B9c (2.6 mg/kg) or placebo (0.9% saline) beginning either 1 hr or 3 hr after the onset of a 90 min MCAO. The dose selected for NHPs was approximated from calculations of a "primate equivalent dose" extrapolated from prior doses used in rat studies and was based on normalization to interspecies differences in body surface area.

Animals were transferred to the MRI scanner within 15 min of MCAO and all underwent perfusion imaging to quantify the brain volume deprived of blood flow during MCAO (tissue-at-risk). Additionally, MR angiography (MRA) was conducted to confirm MCAO. A second MRA was performed after the 90 min MCAO was terminated to confirm reperfusion of the MCA, followed by diffusion imaging at 4 h. Animals were then awakened and allowed to recover. They were re-anaesthetized and re-imaged at 24 h and at 30 days. NHPSS scores were assigned within 8 h of MCAO and up to 30 days, and the remaining neurological tests were conducted on days 7 and either 14 or 30.

There were no differences in physiological parameters between groups in the experiments, or in the volume of tissue at risk between the drug and placebo groups as determined by perfusion imaging within 15 min of MCAO.

We conducted neurological assessments throughout the 14 to 30d observation periods using the non-human primate stroke scale (NHPSS) and, in some cases, a sensorimotor battery of tasks including the Hill and Valley Task, two-tube choice task and six well task. The NHPSS is a composite of ratings analogous to the NIH Stroke scale used in human stroke trials. A score of 41 points represents severe bilateral neurological impairment and 0 is normal. The remaining tests measure a combination of overall strength of the extremity, fine motor function and the influence of a hemi-neglect or visual field defect.

Tat-NR2B9c Treatment Reduces Brain Ischemia and can Extend the Time Window for Reperfusion Therapy Beyond the Current Useful 4.5 Hour Window for the Use of tPA.

Currently, the only widely approved treatment for acute ischemic stroke is reperfusion of occluded brain arteries using the intravenous infusion of the fibrinolytic agent, rt-PA (recombinant tissue plasminogen activator). Conventional reperfusion with intravenous rt-PA is most beneficial in improving clinical outcomes when administered within 90 min after stroke onset, and benefit decreases thereafter until it is marginal or nil at 4.5 h. This narrow window for the utility of reperfusion limits the number of patients who might benefit. Thus one potential application of early treatment with a neuroprotectant is to extend the interval during which clinical benefit may be obtainable from reperfusion therapy. Neurosurgeons and neurointerventionalists can use reperfusion therapy outside of the standard window if the condition of the brain indicates there is still useful brain to save and it would be safe to do so without risking a hemorrhage. To examine this, we evaluated in the NHPs whether administration of Tat-NR2B9c 60 min after MCAO onset might improve stroke outcome when reperfusion is delayed until the 4.5 h time point, at which i.v. rt-PA is no longer of significant benefit in humans (see also Cook et al., Nature. 483, 213-7 2012).

Six macaques were subjected to a permanent MCAO, and were treated either with Tat-NR2B9c or with placebo beginning at 5 minutes after ischemia onset. The animals were placed in the MRI scanner, and DWI MRI scans were obtained every 15 min (FIG. 2A). The volume of brain in which DWI hyperintensity was detectable increased over time in both groups. However, treatment with Tat-NR2B9c attenuated the rate of this increase by about twofold (FIG. 2A; time constants=2.20±0.28 h and 4.50 t 0.54 for control and Tat-NR2B9c, respectively; p=0.019). Even after a 4.5 hour MCAO, Tat-NR2B9c treated animals showed significant reduction in infarct size by MRI and T2 scans at 48 hours and 7 days (FIG. 1B-D). Moreover, within the ischemic volume, the DWI intensity in brains of Tat-NR2B9c treated animals remained lower than that of untreated controls, suggesting that tissue within the infarct volume maintained better integrity (FIG. 2B). These data provide evidence that there remains brain that can be salvaged and administration of reperfusion drugs or therapy would be likely to improve reperfusion and survival of brain tissues at times when they would not normally be considered due to being outside of the effective time window. They also provide evidence that Tat-NR2B9c can extend the useful time for reperfusion of the brain to save the remaining tissue.

Tat-NR2B9c Significantly Reduces Infarct Volumes and Neurological Deficits in Non Human Primates Subjected to a 90 Minute Stroke.

A subsequent study looking at the effect of Tat-NR2B9c when given after a 1 hour after an ischemic stroke was tested in this model. Twenty macaques were randomized to receive a 10 min intravenous infusion of Tat-NR2B9c (2.6 mg/kg) or placebo (0.9% saline) beginning 1 h after the onset of a 90 min MCAO. The dose selected for NHPs was approximated from calculations of a "primate equivalent dose" extrapolated from prior doses used in rat studies and was based on normalization to interspecies differences in body surface area.

Animals were transferred to the MRI scanner within 15 min of MCAO and all underwent perfusion imaging to quantify the brain volume deprived of blood flow during MCAO (tissue-at-risk). Additionally, MR angiography (MRA) was conducted to confirm MCAO. A second MRA was performed to confirm reperfusion after the 90 min MCAO, followed by diffusion imaging at 4 h. Animals were then awakened and allowed to recover. They were re-anaesthetized and re-imaged at 24 h and at 30 days. NHPSS scores were assigned within 8 h of MCAO and up to 30 days, and the remaining neurological tests were conducted on days 7 and 30.

Four of 10 animals receiving placebo died within 48 h of their strokes due to brain swelling and uncal herniation. Three animals treated with Tat-NR2B9c died as a result of surgical/anesthetic complications unrelated to stroke or to drug. None was excluded from the "intent-to-treat" (ITT) analysis. All missing data due to early mortalities were imputed to reflect the largest possible infarct volumes and worst neurological scores. Although this approach biases against detecting a significant treatment effect, it is the most conservative, and most reflective of that employed in human clinical trials.

Figure 6:
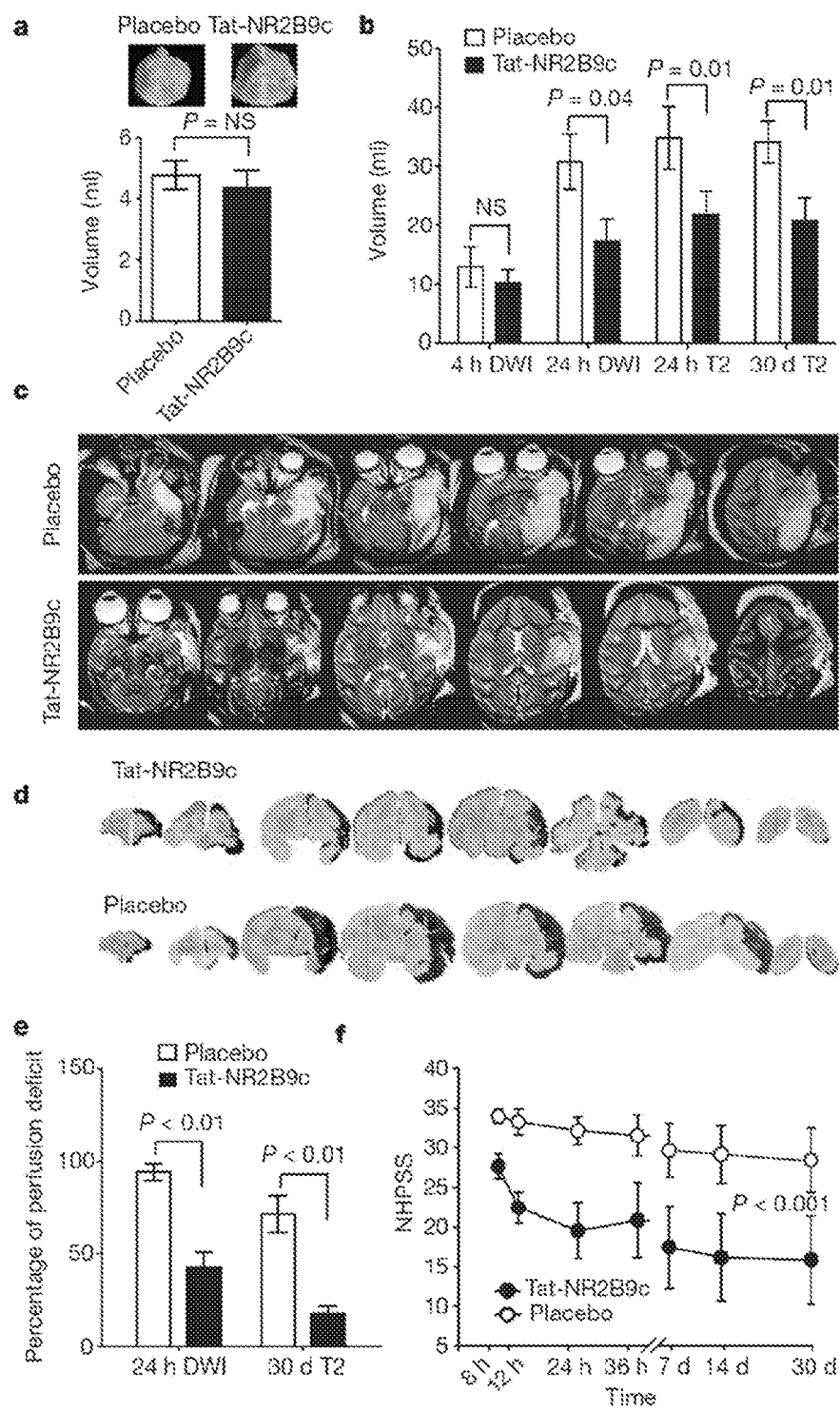
FIG. 6: A: Volumes of perfusion defects at baseline. B: Analysis of stroke volumes as measured by DWI and T2 imaging over 30 days. C: Representative T2-weighted images of strokes incurred in placebo and drug treated animals 24 hr after MCAO. D: Representative serial histological sections from NA-1 (Tat-NR2B9c) and placebo treated animals at 30 days stained with haematoxylin and eosin. E: Stroke volumes calculated using 24 hr DWI volumes and 30-day T2-weighted volumes. F: NHPSS over the 30 day observation period.

There were no differences between the drug and placebo groups in physiological parameters or in the volume of tissue at risk as determined by perfusion imaging within 15 min of MCAO (FIG. 6A). However, by 24 h, animals treated with Tat-NR2B9c exhibited a significant reduction in infarct volume as compared with placebo by DWI imaging (44.0% reduction; p=0.039; FIG. 6B) and by T2-weighted imaging (37.4% reduction, p=0.010; FIG. 6B, C). This reduction in infarct volume persisted as reflected by the 30d T2-weighed MRI scans (38.7% reduction, p=0.013; FIG. 6C) and by histological evaluation at 30d (FIG. 6D; 59.3% and 73.6% reduction in infarct volume when evaluated by ITT and with early mortalities removed, respectively; p<0.001). Because NHPs, like humans, may have variable infarcts after MCAO, the infarct volume of each animal was normalized to its MRI perfusion defect measured within 15 min of MCAO. This normalization revealed that treatment with Tat-NR2B9c reduced infarcts by 55% of the volume at risk by 24 h as gauged by DWI imaging, and by 70% at 30d as measured with T2-weighed MRI (FIG. 6E). Infarct volumes calculated from the 24 h DWI MRI correlated well with those obtained from the 30d histological analysis (R=0.691, p<0.01).

We conducted neurological assessments throughout the 30d observation period using the non-human primate stroke scale (NHPSS) and a sensorimotor battery of tasks including the Hill and Valley Task, two-tube choice task and six well task. The NHPSS is a composite of ratings analogous to the NIH Stroke scale used in human stroke trials. A score of 41 points represents severe bilateral neurological impairment and 0 is normal. The remaining tests measure a combination of overall strength of the extremity, fine motor function and the influence of a hemi-neglect or visual field defect.

Animals treated with Tat-NR2B9c exhibited improved NHPSS scores from the earliest assessment at 8 h post-ischemia onset and throughout the 30d observation period (P=0.018, Two way repeated measures ANOVA; FIG. 6F). Performance in the 2 tube choice task returned to pre-stroke levels in animals treated with Tat-NR2B9c, but remained completely impaired in the placebo group, suggesting that brain salvage prevented "extinction", the tendency for attention to items in ipsilesional hemispace to overshadow attention to items in contralesional hemispace. Treatment with Tat-NR2B9c also significantly improved the performance of animals in the 6-well and the Hill and Valley Staircase tasks in the left upper extremity. Right upper extremity performance also showed improvements, suggesting overall improved attention and perceptual ability.

Tat-NR2B9c is Effective in Reducing Infarct Size and Neurological Deficits in Severe Strokes We next demonstrated the efficacy of Tat-NR2B9c in strokes that lasted longer than the limit of effectiveness of reperfusion with intravenous tPA, 4.5 hours. Twelve macaques were randomized to receive a 10 min intravenous infusion of Tat-NR2B9c (2.6 mg/kg) or placebo (0.9% saline) beginning 1 h after the onset of a 4.5 h min MCAO. Otherwise, methods were similar to our first study except for the timing of MRI scans and that final imaging and neurological assessments were conducted at 7 days.

Figure 7:
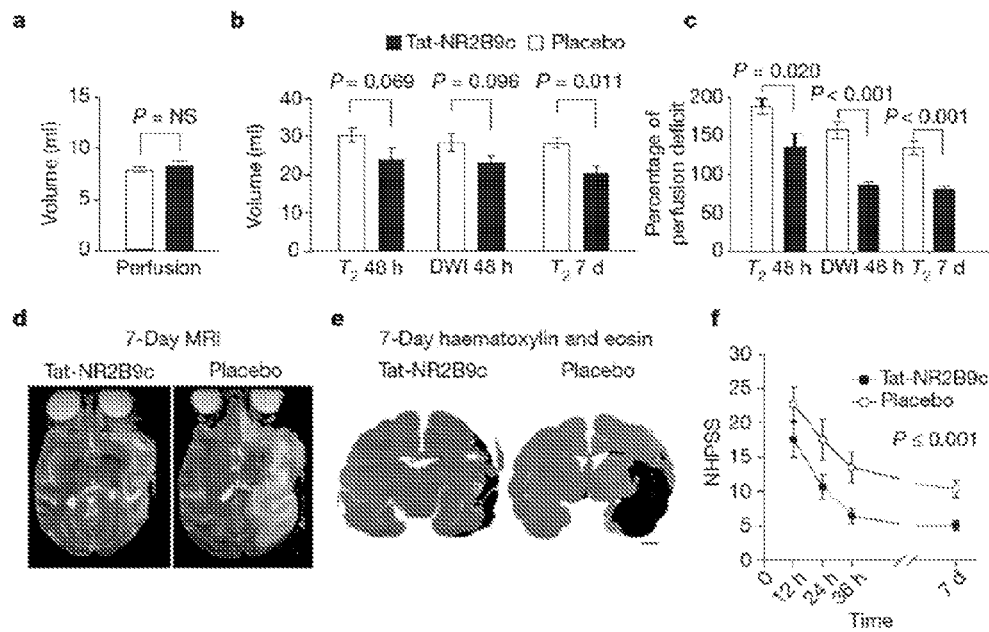
FIGS. 7A-F: A: volume of perfusion defects. B: Stroke volumes as measure by DWI and T2 MRI over 7 days. C: Stroke volumes from 48 hr DWI and T2- and 7-day T2-weighted MRI scans normalized to each animal's initial perfusion deficit. D: Representative 7-day MRI. E: Representative 7-day histology. F: NHPSS scores over the 7-day observation period.

There were no mortalities and no differences between the drug and placebo groups in physiological parameters or in the volume of tissue at risk upon MCAO (FIG. 7A). However, despite the prolonged ischemic interval, animals treated with Tat-NR2B9c exhibited a significant reduction in infarct volumes as compared with placebo when evaluated by T2 and DWI imaging at 48 h and by T2-weighted imaging at 7 days (FIGS. 7B-E). Moreover, animals treated with Tat-NR2B9c exhibited improved NHPSS scores from the earliest assessment at 12 h post-ischemia onset and throughout the 7D observation period (P=<0.001; Two way repeated measures ANOVA; FIG. 7F), and trended to better performance in the 6-well and the Valley Staircase tasks. These results suggest that early treatment with Tat-NR2B9c may increase the window during which reperfusion may have functional benefits, even in the model of severe MCAO in which collateral circulation is limited and the penumbra is small. The size of the benefit of treatment at 4.5 h post-stroke as gauged by MRI and by neurological evaluations suggest a potential for utility of early neuroprotection to extend the benefits of reperfusion therapy even beyond the 4.5 h window.

Tat-NR2B9c is Effective at Reducing Ischemia and Neurological Deficits Following Stroke when Given 3 Hours after the Onset of Stroke Although treatment with a neuroprotectant within 60 min of stroke onset is feasible in a small subset of patients, extending the therapeutic window of administration would benefit a much greater proportion of stroke victims. Thus we determined whether administering Tat-NR2B9c at 3 h after stroke onset is beneficial in the setting of a prolonged MCAO. In humans, reperfusion with i.v. rtPA administered 3 h after stroke onset is beneficial even in the absence of neuroprotection. This attests to the existence of a salvageable penumbra at this time in many patients. We reproduced this clinical scenario experimentally by using the MCAO model in which the NHPs exhibit a significant PWI/DWI mismatch (penumbra) at 3 h. Like in humans, such a mismatch progresses to infarction in the absence of treatment.

Figure 8:
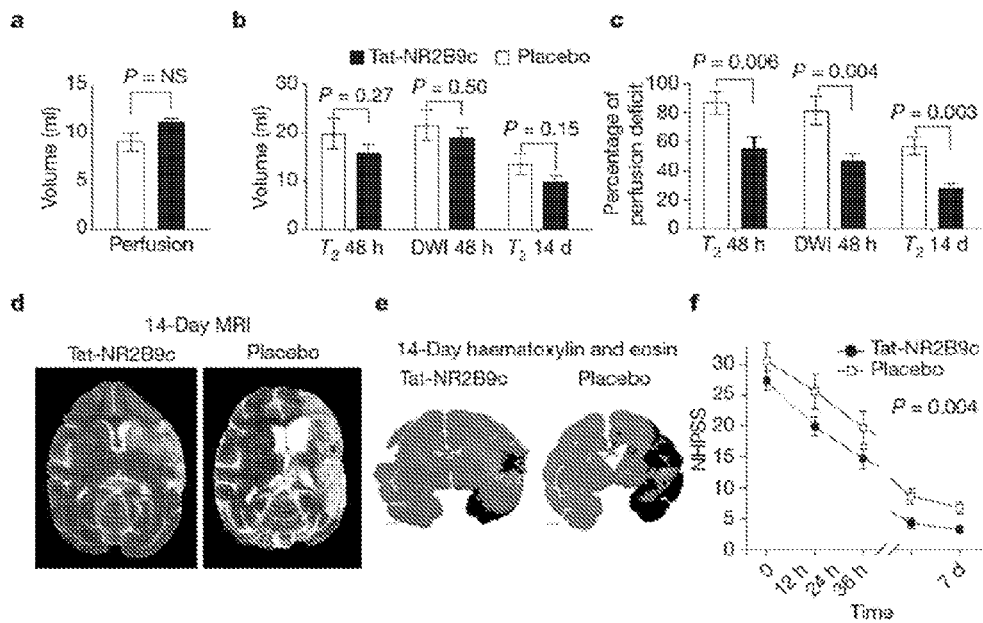
FIGS. 8A-F: A: volume of perfusion defects. B: Stroke volumes as measure by DWI and T2 MRI over 14 days. C: Stroke volumes from 48 hr DWI and T2- and 14-day T2-weighted MRI scans normalized to each animal's initial perfusion deficit. D: Representative 14-day MRI. E: Representative 14-day histology. F: NHPSS scores over the 14-day observation period.

Twenty-four macaques were randomized to receive a 10 min intravenous infusion of Tat-NR2B9c (2.6 mg/kg) or placebo (0.9% saline) beginning 3 h after the onset of a 3.5 h MCAO. Other methods were unchanged, except that final imaging and neurological assessments were conducted at 14 days. There were no mortalities and no differences in physiological parameters or in the volume of tissue at risk upon MCAO between the groups (FIG. 8A). However, despite both the prolonged ischemic interval and the delayed treatment with Tat-NR2B9c, drug-treated animals exhibited significant reductions in infarct volumes as compared with placebo as evaluated by anatomical (MRI) criteria at 48 h and 14 days (FIG. 8B-E). The NHPs treated with Tat-NR2B9c also exhibited improved NHPSS scores throughout the 14d observation period (P=0.004 Two way repeated measures ANOVA; FIG. 8F), and tended to better performance in the 6-well and the Valley Staircase tasks. Thus, treatment with Tat-NR2B9c 3 h after stroke onset is effective in reducing stroke damage in NHPs. As this therapeutic window is practical in stroke victims, treatment with a PSD95 inhibitor can constitute a clinically-practicable therapeutic strategy, and be more effective that the use of reperfusion alone.

Conclusions

Tat-NR2B9c can effectively reduce the severity of the damage following stroke in higher order brains like monkeys and humans. Examining the MRI DWI and T2 images at time points following the stroke demonstrates that the areas of ischemia are significantly less damaged than those in untreated animals. In addition to the reduction in volumes of the lesions, this is suggested by less intense images by DWI-MRI and reduced signal intensity on the T2 images. These data provide evidence that there is still brain left to save and that reperfusion therapy can still allow blood to penetrate into and act upon a greater portion of the brain that it would otherwise be able to without Tat-NR2B9c treatment. Thus, reperfusion therapy, especially with drugs like tPA, is able to better penetrate and be effective at further increasing the blood flow to the affected areas of the brain.

Non-Human Primate Methods

Stroke Model:

Animals were anesthetized (Isoflurane 1.0-2.5%), intubated and ventilated. Non-invasive monitoring included BP by leg cuff, end-tidal CO2, O2 saturation, ECG and temperature by rectal probe. Temperature was maintained (37±0.5 C) by heating blanket. A femoral arterial line was used to monitor BP and blood gases. MCAO in cynomolgus macaques (3.0-4.0 kg) was performed using a right pterional craniotomy and occluding the right MCA in the Sylvian fissure with a 5 mm titanium aneurysm clip distal to the orbitofrontal branch and origin of lenticulo-striate arteries.

Defining Ischemic Penumbra Tissue:

Penumbra tissue was operationally defined as tissue which is not yet infarcted at the time of tissue harvest, but which consistently goes on to later infarction. Because the penumbra might be variable in macaques, eight 2×2 mm biopsies were taken at either 1 h or 6 h post MCAO from cortex across the entire MCA vascular distribution ipsilateral to the stroke and also contralateral to the stroke from sites mirroring those taken from ischemic cortex. Biopsied positions were photographed. To determine which of the 8 biopsies represent penumbral tissue, the animals were transferred to a 7T MRI scanner and diffusion weighted (DWI), T2 and perfusion imaging was performed within 15 minutes after the biopsy and at 5.75 h. Penumbra tissue at 1 h was defined as tissue devoid of infarction that progressed to infarction at 5.75 h by DWI. Penumbral tissue at 6 h was defined as tissue within the confines of the MR perfusion defect but without demonstrated DWI or T2 hyperintensity. The use of MRI to define the penumbra of NHPs is essential as the amount of salvageable tissue shrinks by 6 h.

General MRI Procedures:

Imaging was performed on a 7-Tesla Bruker BioSpec system running Para vision 4.0 software and using a B-GA20S gradient coil. A 15.5 cm inner diameter quadrature transmit/receive volume coil was used for NHP scans. NHPs were intubated, ventilated and imaged prone. Physiological monitoring was maintained throughout. The protocol provides stacks of 2D T2-weighted, perfusion and diffusion-weighted images in an axial plane. T2-weighted imaging uses the RARE method, also termed fast-spin echo (TE/TR=84/5000 ms, rare factor-14, 225×225 matrix over a 9 cm field-of-view for 400×400×1500 micron resolution). Diffusion-weighted imaging uses a spin-echo multi-shot echo-planar imaging technique (TE/TR=32/10000 ms, 9 EPI shots, 250 kHz bandwidth, 3 orthogonal diffusion directions at b=1000 s/mm2, 10 averages with a 180×180 matrix over a 9 cm field-of view for 500×500×1500 micron resolution). Perfusion imaging was performed using a dynamic, contrast enhanced, susceptibility-weighted perfusion method (T2*EPI, TE=18 ms, 2 EPI shots, 2-sec temporal resolution, and 90 repetitions, 180×180 matrix over a 9 cm field of view for 700×700×1500-micron resolution over 5 contiguous slices). For perfusion scans, gadolinium (0.1 mmol/kg) bolus was injected intravenously, starting on the third repetition with a total injection time of 7-sec through a peripheral intravenous. Diffusion images are post-processed in MATLAB (Natick, Mass., USA) to generate an average image from three b=1000 s/mm2 images and to calculate an Apparent Diffusion Coefficient (ADC) map. Stroke volumes were calculated using ITK-Snap contouring software (Pittsburgh, Pa., USA) with stacks of average diffusion images reconstructed in 3-dimensions. Perfusion imaging was processed using PerfTool software to produce cerebral blood flow maps.

Experimental Design and Statistical Analysis:

The stroke experiments were performed in compliance with the "recommendations for ensuring good scientific enquiry" of the Stroke Therapy Academic Industry Roundtable (STAIR) committee. A sample size of 10 animals/groups was based on the desire to detect a 40% difference in infarct volumes between drug and placebo based on the 30d T2 weighted MRI at a power of 0.8, alpha=0.05 and an assumed standard deviation of 30% of group means. Primary analysis was based on an intent-to-treat approach, with no exclusions of any animals enrolled. 20 cynomologus macaques were block-randomized to treatment with drug or placebo (vehicle only). The investigators responsible for the induction, maintenance, and reversal of ischemic, for decisions regarding the care of (including the early sacrifice of) experimental animals, and assessment of all outcomes were blinded to the experimental group to which an animal belonged. Differences between groups were measured using Student's t-test, or repeated-measures ANOVA, as required. Missing values due to premature death or inability to complete a task were imputed to reflect the worst score achievable on the task, or the maximum possible stroke volume as defined by largest infarct volume achieved across all animals.

Neurological Assessments:

These were conducted using the previously validated non-human primate stroke scale (NHPSS) and a sensorimotor battery of tasks including the Hill and Valley Task, two-tube task and six well task. The NHPSS score is a composite of ratings of state of consciousness, defense reaction, grasp reflex, extremity movement, gait, circling, bradykinesia, balance, neglect, visual field cut/hemianopsia and facial weakness, many of which are also incorporated in the NIH Stroke Scoring system in humans. From a total of 41 points. 0 corresponds to normal behavior and 41 to severe bilateral neurological impairment. The remaining tests were modified from assays developed for the common marmoset (*Callithrix jacchus*) as described elsewhere. In additional to evaluating finer sensorimotor functions they also test extinction and perceptual spatial impairment/neglect. In pilot experiments in 5 macaques subjected to a 90 min MCAO, NHPSS results demonstrated an initial peak in score (mean 36.3, SEM=5.7) that persisted for the first 36 hours and then gradually dropped to a plateau between 14 and 30 days (mean=14.36, SEM=3.2). Sensorimotor testing revealed that animals had severe left spatiotemporal neglect and left hemiparesis that showed minor recovery over time at 7 and 30 days following stroke. These deficits were evident as significant delays in completion of 6 well (mean delay of 7.8× and 5.33× baseline) and Hill and Valley tasks for the left arm (mean delay of 8.2× and 6.4× baseline on Valley segment and mean delay of 7.6× and 5.8× baseline on Hill segment).

Example 2: PSD-95 Inhibitors Freeze Ischemic Penumbra Evolution on Perfusion/Diffusion Weighted MRI The purpose of this example was to demonstrate that neuroprotection using a PSD-95 inhibitor is feasible without cerebral blood flow augmentation (reperfusion) in experimental permanent MCAO.

Methods: Rats were subjected to pMCAO and were treated 1 h thereafter with a 5 minute intravenous infusion of the PSD-95 inhibitor Tat-NR2B9c (7.5 mg/kg) or saline. Perfusion MRI (PWI) and diffusion MRI (DWI) were obtained with a 4.7T Bruker system at 30, 45, 70, 70, 120, 150 and 180 minutes post pMCAO to determine cerebral blood flow (CBF) and apparent diffusion coefficient (ADC) maps. At 24 hours animals were neurologically scored, sacrificed, and brains sectioned and stained with TTC to ascertain infarct volumes correct for edema. The effect of Tat-NR2B9c on ATP levels were measured in vitro in neurons subjected to OGD as described (Aarts et al. (2002), supra) and ATP levels were assessed using a CellTiter-Glo Luminescent Cell Viability Assay according to manufacturer's instructions (Promega, Madison, Wis.).

Results: Blood gases, electrolytes, and blood glucose did not differ between the two groups. Neuroscores at 24 hours showed the Tat-NR2B9c group had a significantly improved neuroscore compared to placebo. FIG. 3 indicates the absolute mismatch between CBF and ADC-derived lesion volumes. Relative to placebo animals, the ADC/CBF mismatch lesion volumes were significantly larger starting at 90 minutes after occlusion in the Tat-NR2B9C group. The region of interest analysis of the relative CBF values in the core and cortical penumbra regions showed no significant change in relative CBF between time points in either treatment group, indicating no effect of Tat-NR2B9c treatment on CBF.

Figure 5:
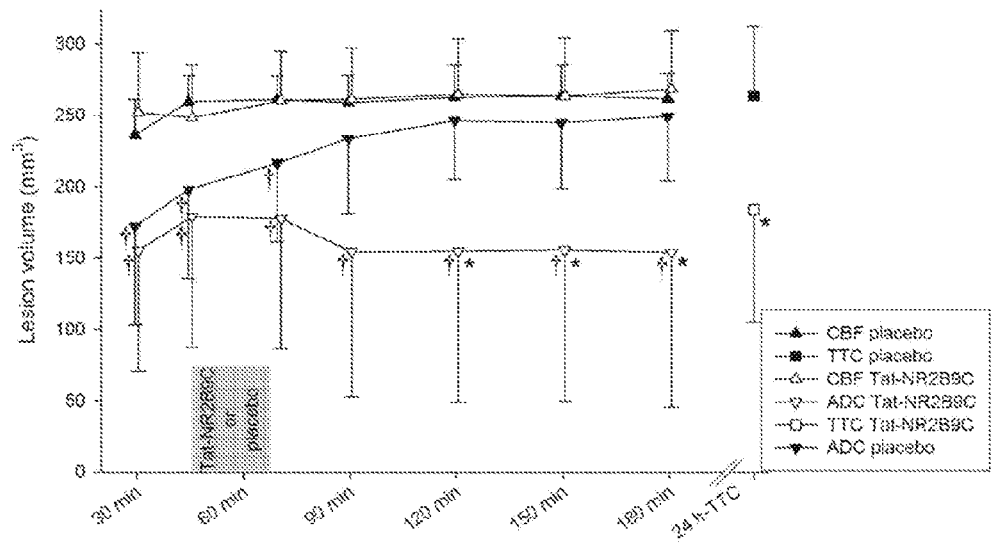
FIG. 5: Demonstration that NA-1 (Tat-NR2B9c), when administered as a single dose after a stroke, can halt the development of lesions in the brain as assessed by Magnetic Resonance Imaging (MRI). This efficacy does not act through the modification of cerebral blood flow.

The spatiotemporal evolution of the ischemic stroke described by threshold-derived ADC and CBF lesion volumes, correlated well to the TTC-derived lesion volumes in placebo treated animals. In Tat-NR2B9c treated animals, the ADC lesion volume increased from 25 minutes to 45 minutes post MCAO as in the placebo group. However, at the 70 minute time point, just after initiation of Tat-NR2B9c drug, the increase was attenuated. At 120 minutes and beyond, the ADC lesion in Tat-NR2B9c-treated animals remained significantly smaller than in placebo-treated rats. CBF-derived volumes and TTC infarct volumes were significantly smaller in Tat-NR2B9c animals. FIG. 5 indicates the absolute mismatch between CBF and ADC derived lesion volumes. Relative to placebo animals, the ADC/CBF mismatch lesion volumes were significantly larger starting at 90 minutes following inclusion in the Tat-NR2B9c group. These results suggest that Tat-NR2B9c does not reduce infarct size or improve outcome by shrinking the size of the ischemic penumbra, as would occur if per-infarct blood flow were augmented by the treatment. Rather, it suggests that Tat-NR2B9c works as a neuroprotectant that enhances the resilience of ischemic tissue to existing ischemia.

Figure 4:
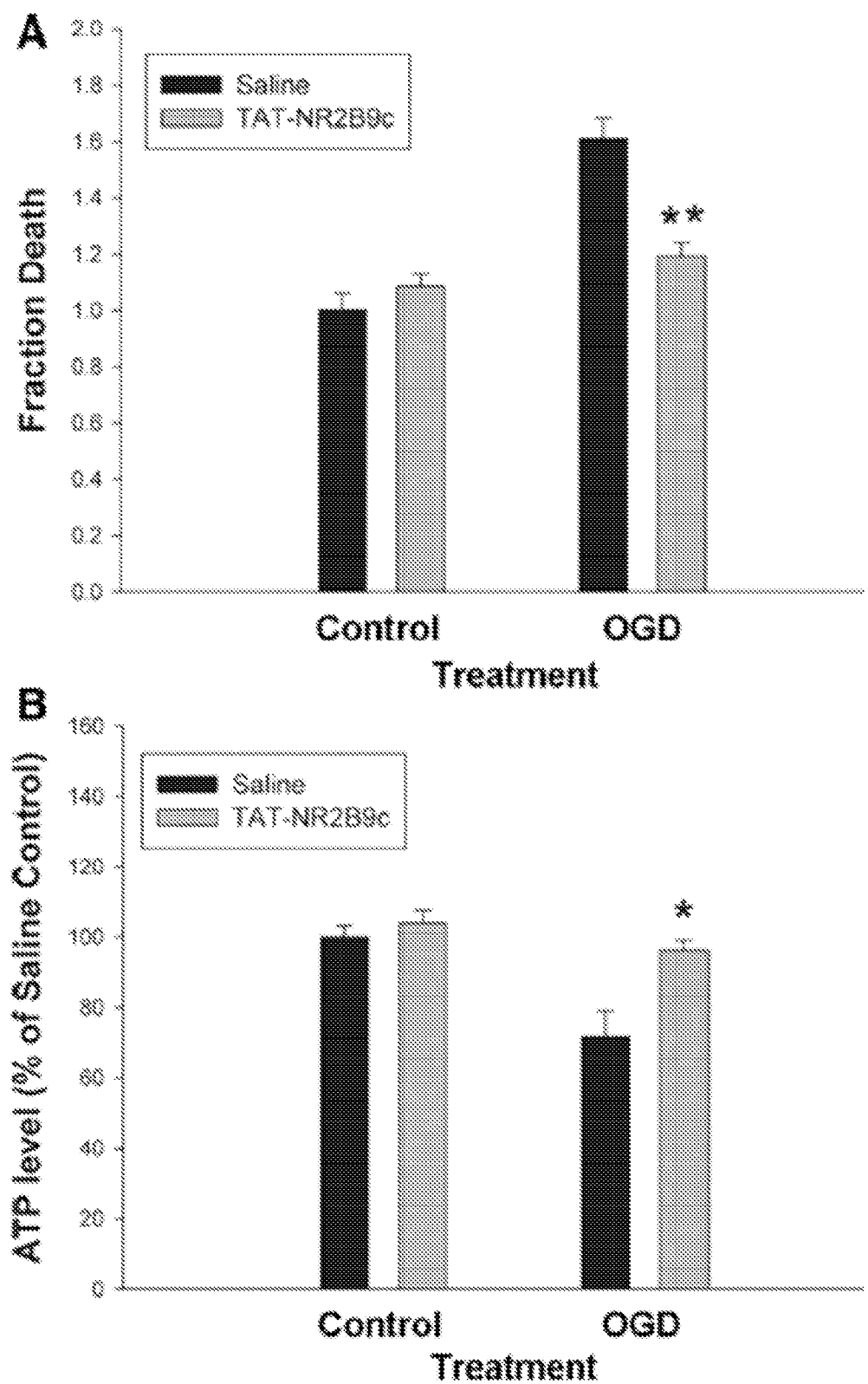
FIGS. 4A, B. Tat-NR2B9c reduces intracellular ATP depletion and protects mouse cortical neurons against cytotoxicity induced by oxygen-glucose deprivation (OGD). (A) Fraction of cell death as measured 20 hours after OGD by propidium iodide labeling method. (B) Intracellular ATP concentration from cortical neurons determined by a chemiluminescent ATP detection assay, expressed as % ATP concentration relative to normoxic control samples.

Primary neuronal cultures treated with 100 nM Tat-NR2B9c demonstrated no significant in cell death or ATP levels compared to saline controls un normoxic conditions. However, pretreated with 100 nM Tat-NR2B9c resulted in a 26% reduction in cell death as compared to saline controls 20 hours after OGD (FIG. 4A). ATP levels were 34% greater in Tat-NR2B9c treated cultures 1 hour after OGD compared to saline treated cultures (FIG. 4B).

Discussion: Administration of Tat-NR2B9c 60 minutes after MCAO in rats or mice resulted in a significant reduction in ADC hypointensity volume and correlated with a reduction in infarct volume by TTC. Reduction in stroke volume was associated with significant improvement in neurological scores 24 hours after MCAO. These anatomical and neurological improvements in stroke outcome after pMCAO were achieved without affecting cerebral blood flow, establishing that stroke therapy is achievable by neuroprotection even without blood flow augmentation. Thus, it is expected that coupling treatment with PSD-95 inhibitors to reperfusion strategies, either physical or therapeutic, are likely to further enhance salvage or neuronal tissues or the brain following stroke.

Following onset of ischemia, there is a rapid drop in intracellular ATP levels in neurons and glia that is associated with disruption of homeostatic mechanisms, failure of cellular function and cell death. As PSD-95 inhibitor treatment resulted in decreased ATP depletion. These results constitute the PSD-95 inhibitor treatment preserves the ischemic penumbra providing a viable approach to extending the therapeutic or temporal window of reperfusion therapies.

Example 3: A Single 4-5 Minute Infusion of Tat-NR2B9c is Sufficient to Disrupt the NMDAR:PSD95 Complex in Rodent Brains Subjected to Stroke Methods Summary:
Postsynaptic Density-95 Inhibitors Tat-NR2B9c is a synthetic peptide comprised of the 9 c-terminal amino-acids of the NR2B subunit (KLSSIESDV) fused to the cell membrane protein transduction domain of the HIV-1-Tat protein (YGRKKRRQRRR; Tat). A control incapable of binding PSD95 is a similar peptide in which the 3 terminal amino acids of the NR2B C-terminus sequence were switched from SDV to ADA this control is termed "ADA" peptide. The peptides were administered intravenously in saline over 4 to 5 minutes by an individual blinded to the identity of the compound and to its dose.

Animals

Adult male Sprague-Dawley rats (250 to 300 g; Charles River Laboratories, Sherbrooke, Quebec, Canada) were used according to procedures approved by the institutional animal care committees. All experiments were performed on unfasted animals.

Surgical Preparation:

For permanent pial vessel occlusion (3PVO), rats were anesthetized with 100 mg/kg ketamine, 2 mg/kg acepromazine, and 50 mg/kg xylazine. Rats were intubated and ventilated (60 strokes/min, tidal volume of 30 to 35 mL). Mean arterial blood pressure, blood gases, pH, and glucose were monitored with a left femoral artery catheter. Drug delivery was through the tail vein.

Experimental Procedure.

Animals were subjected to 3PVO ischemia. One hour thereafter, they were injected with Saline, 3 nmol/g of Tat-KLSSIEADA (SEQ ID NO:76), or with 0.3 nmol/g, 3 nmol/g and 10 nmol/g of Tat-NR2B9c (Tat-KLSSIESDV). After a further hour, the brain cortex was quickly harvested from the ipsilateral (stroke) side, and from the side contralateral to the stroke. Sham treated animals had the craniotomy only, but no stroke or drug infusion. Co-IP experiments were then conducted on the harvested tissue using routine methods. Following CoIP with anti-NR2B or anti-PSD95 antibodies, the blots were probed with the indicated antibodies (anti NR2B, PSD95 and Src). Densitometric analysis of bands was performed using Image J software. To measure the effects of a treatment on the CoIP of associated proteins, the levels of each protein on the blot were first normalized to the levels of the protein that was immunoprecipitated (PSD95 or NR2B), and then levels from the ipsilateral (stroke) side were normalized to the levels on the contralateral side.

Figure 9:
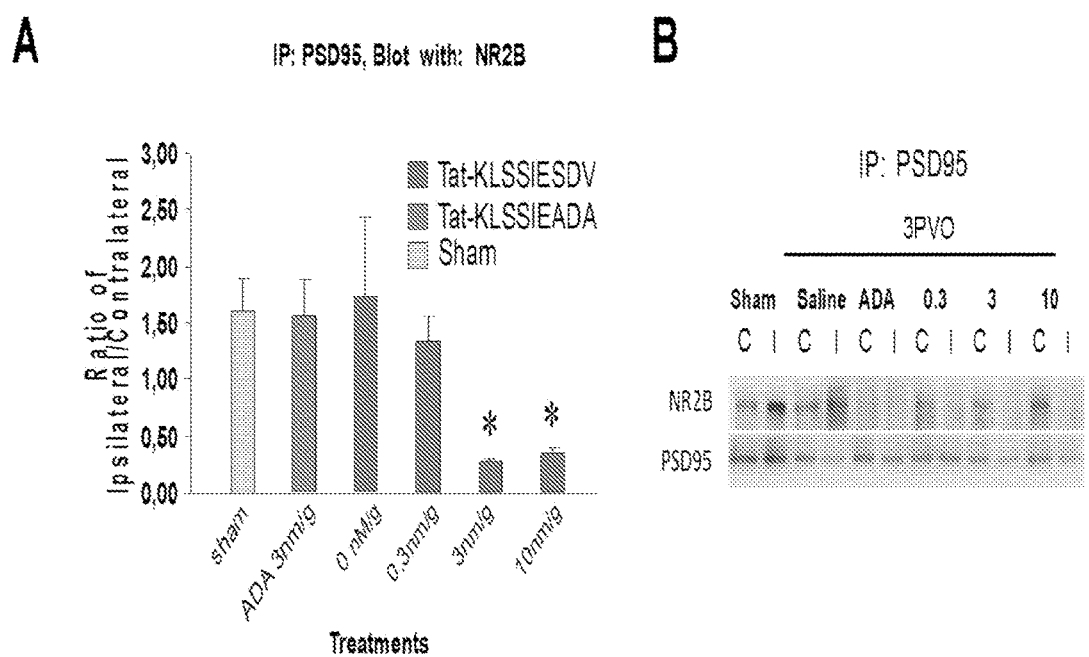
FIGS. 9A, B: A: Graph showing the ratio of PSD-95: NMDAR co-immunoprecipitation between the ipsilateral and contralateral hemispheres of rats following a stroke and treatment with NA-1 (Tat-NR2B9c). B: Example immunoblots showing the amount of NMDAR immunoprecipitated with an anti-PSD-95 antibody in the presence of various concentrations of NA-1 or controls.

Results:

The experiment was conducted in 5 replicates. Tissue for each replicate was obtained from a 6 separate rats (one per condition). In each replicate, tissue was obtained from both the stroke side (ipsilateral) and the contralateral hemisphere. There was no effect of sham treatment (no stroke and no drug infusion) on the co-immunoprecipitation of PSD95 and NR2B as evaluated by IPs performed with antibodies to either protein (FIGS. 9A-B shown as example). Similarly, the treatment with the control peptide Tat-KLSSIEADA had no effect on the co-IP of PSD95 and NR2B. However, treatment with Tat-KLSSIESDV inhibited the co-IP of PSD95 with NR2B in a dose-dependent manner (FIGS. 9A-B). The degree inhibition the co-IP of PSD95 with NR2B paralleled the potency of Tat-NR2B9c in inhibiting strokes, where 0.3 nmol/g is ineffective in reducing the size of the infarction in this model of stroke and doses of 3 or 10 nmol/g were effective. Specifically, treatment with an Tat-NR2B9c dose of 0 nM/g or 0.3 nM/g, which was ineffective in reducing stroke size, did not significantly inhibit the association of PSD95 and NR2B. By contrast, treatment with Tat-NR2B9c at a dose of 3 nM/g or 10 nM/g, which are effective in inhibiting stroke damage also significantly inhibited the association of NR2B with PSD95. As a further control, tissue that was immunoprecipitated with either PSD95 or with NR2B was probed with antibodies against the NMDAR-associated protein kinase Src, a major regulatory protein in the NMDAR signaling complex25. Treatment with 10 nM/g Tat-NR2B9c, which dissociates NR2B from PSD95 (FIG. 9A-B) had no effect on the association of either PSD95 or of NR2B with Src (not shown). This indicates that the actions of Tat-NR2B9c in inhibiting NR2B/PSD95 interactions are specific, as Tat-NR2B9c had no effect on a similar interaction of either protein with Src.

Conclusions:

First, Tat-NR2B9c gets into the brain on the side of the stroke and is able to dissociate pre-formed NR2B/PSD95 complexes in the ischemic brain when administered after a stroke. Second. Tat-NR2B9c is able to achieve this in a dose-dependent manner. Third, the doses at which Tat-NR2B9c achieves a significant dissociation of pre-formed NR2B/PSD95 complexes in the brain correspond to doses at which Tat-NR2B9c is neuroprotective in the same animal stroke model. Fourth, the doses at which Tat-NR2B9c is unable to achieve a significant dissociation of pre-formed NR2B/PSD95 complexes in the brain are also doses at Which Tat-NR2B9c at Which Tat-NR2B9c is not neuroprotective in the same animal stroke model. Fifth, Tat-NR2B9c achieves its effects on NR2B/PSD95 complexes selectively (i.e., this is not a non-specific effect on NMDAR signaling complex molecules).

Figure 10:
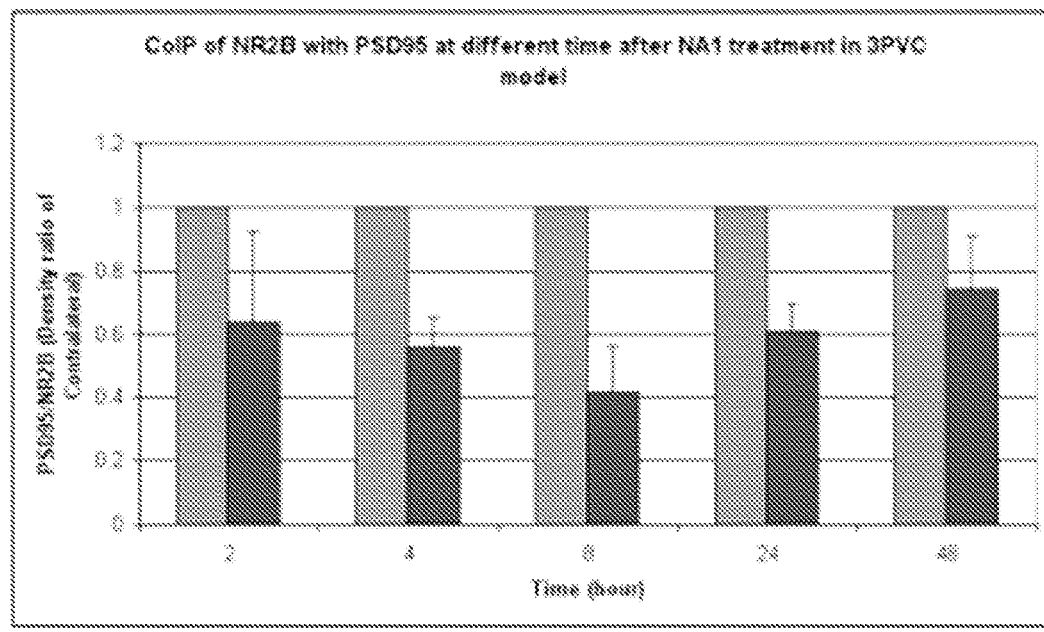
FIG. 10: Graph showing the ratio of PSD-95:NMDAR co-immunoprecipitation between the ipsilateral and contralateral hemispheres of rats at different timepoints following a stroke and treatment with NA-1 (Tat-NR2B9c).

A second study was performed with the same model and treatment conditions to explore the time course of the disruption of the PSD95-NMDAR complex in neurons located in regions of the brain subjected to a stroke. As with the previous study, rat brains were harvested at 2, 4, 8, 24 or 48 hours after PLAL vessel occlusion to induce a stroke. FIG. 10 demonstrates that the NMDAR:PSD-95 complex is disrupted for at least 8 hours following a single intravenous infusion of Tat-NR2B9c and potentially 24-48 hours. Thus, there is a wide window of time between when Tat-NR2B9c could be administered to a patient and when the patient may benefit from reperfusion therapy, whether therapeutic or mechanical.

Detailed Materials and Methods

Materials.

NA1 (GMP lot 16511107) and TAT-ADA (YGRK-KRRQRRRKLSSIEADA) (SEQ ID NO:9) were chemically synthesized by Bachem and Gene Script, respectively. All peptides were high-performance liquid chromatography purified to >95%. Peptide stocks (3 mM or 10 mM) were prepared in sterile saline and stored at 4° C.

Antibodies.

Immunoprecipitations and westerns: Mouse anti-NMDA2B (ab28373; Abeam), rabbit anti-PSD95 (2507; Cell Signaling), rabbit anti-NMDA2B (4212, Cell Signaling), mouse monoclonal anti-PSD95 (MA1-046, Thermo), mouse monoclonal anti-Src (ab16885-100) (Abeam). Dynabeads protein G Immunoprecipitation Kit was used for the immunoprecipitations (100.07D, Invitrogen). The secondary antibodies for western blots were peroxidase conjugated AffiniPure F(ab')2 Fragment Goat anti Rabbit IgG antibody (111-036-047) and peroxidase conjugated AffiniPure F(ab')2 Fragment Goat anti Mouse IgG (115-036-006) from Jackson ImmunoResearch Lab Inc.

Three Pial Vessel Occlusion Model of Ischemia.

Male Sprague Dawley rats (n=6 per co-IP experiment) weighing between 250 and 300 g were used for this study. For permanent three pial vessel occlusion (3PVO) was performed as described previously4,26. In brief, rats were anesthetized with a 0.5 ml/kg intramuscular injection of ketamine (100 mg/kg), acepromazine (2 mg/kg), and xylazine (5 mg/kg), supplemented with one-third of the initial dose as required. An anal temperature probe was inserted, and the animal was placed on a heating pad maintained at 37° C. The skull was exposed via a midline incision and scraped free of tissue. Using a dissecting microscope and a pneumatic dental drill, a 6- to 8-mm cranial window was made over the right somatosensory cortex (2 mm caudal and 5 mm lateral to bregma) by drilling a rectangle through the skull and lifting off the piece of skull while keeping the dura intact. The 3 pial arteriolar middle cerebral artery branches around the barrel cortex (were electrically cauterized at 2 spots for per artery through the dura. After the cauterizations, the scalp was sutured. One hour after 3PVO ischemia, rats were administered the treatment drug in a total of ~300 ul of saline over 3 mM through the femoral vein (exact volume to achieve the target mg/kg dose to the animal was determined by weight of the animal) At 1 hour after administration of the treatment drug (2 hours post stroke), rats were euthanized using 3% isoflurane mixed with oxygen.

Preparation of Brain Lysates.

Brains were removed from skull and both the ischemic area of the cortex and an equivalent sample on the contralateral side were quickly harvested. Each brain sample was placed in 350 ul RIPA lysis buffer (Tris-HCL 50 mM, NaCl 150 mM, EDTA 1 mM, SDS 0.1%, Deoxycholic acid 0.5%, NP-40 1% plus complete protease inhibitor cocktail (PhosSTOP phosphatase inhibitor cocktail, Roche)), homogenized and placed on ice.

Co-Immunoprecipitation of NMDAR and its Associated Proteins, Front Rat Cortex.

Rat cortex lysates were incubated on ice for one hour then centrifuged 20 min at 4° C. (12,000 rpm). The supernatants were transferred to new tubes, incubated overnight at 4° C. with 30 ul Dynabeads protein G (Invitrogen) that were pre-loaded with 5 ug of either anti-PSD95 or anti-NMDAR antibodies (per Manufacturer's protocol using wash buffers provided). Dynabead-antibody-antigen complexes were washed four times, and resuspended in 30 ul RIPA buffer+10 ul SDS-PAGE loading buffer (2.4 ml 1M Tris pH 6.8, 0.8 g SDS, 4 ml 100% glycerol, 0.1% Bromophenol Blue, 1 ml beta-mercaptoethanol, q.c. to 10 mL with dH2O). Samples were heated for 10 minutes at 75° C., placed on a magnet to retain the beads and there supernatants were loaded onto an SDS-PAGE gel for analysis.

SDS-PAGE and Western Blotting.

Isolated immunoprecipitates were resolved using 10% SDS-PAGE and subsequently transferred to nitrocellulose membranes. The membranes were probed with anti-PSD95 at 1:1000, then washed and developed using an ECL chemiluminescence kit (Amersham/GE Healthcare). Images were captured using a Luminescent Image Analyzer LAS-3000

(Fujifilm) with exposures from 30 s to 2 min. Membranes were subsequently stripped for 10 minutes at room temperature (1.5% glycine, 0.1% SDS, 1% Tween 20 pH 2.2) and reblocked. Membranes were then re-probed with anti-NMDAR2B (1:1000) and anti-Src antibodies (1:500), washed, developed and images captured as above.

Image Analysis.

Band intensities on images were analyzed by using Image J (NIH). Ipsilateral and contralateral bands were first normalized to immunoprecipitated PSD95 or NR2B levels before generating ratios of band densities between ipsilateral and contralateral immunoprecipitates from the same animal.

Example 4: Tat-NR2B9c and tPA can be Given Concurrently or at Separate Times to Improve Outcomes from Stroke First, an in vitro study was performed to demonstrate that Tat-NR2B9c has no effect on clot lysis and that Tat-NR2B9c does not affect the ability or rate of tPA to release fibrin from clots. Briefly, human plasma containing $^{125}$I labeled fibrinogen was incubated with various concentrations of Tat-NR2B9c. Tat-NR2B9c+1500 ng/ml tPA, or tPA alone in a buffer containing 100 nM NaCL, 30 nM $Na_2HPO_4$, 3 mM nM $NaH_2PO_4$, pH7.4 for 2 hours at 37° C. Quantification of fibrin release from clots was measured by scintillation counting of soluble material. Tat-NR2B9c did not lyse clots, nor did it affect the ability of tPA to release fibrinogen from clots.

Figure 11:
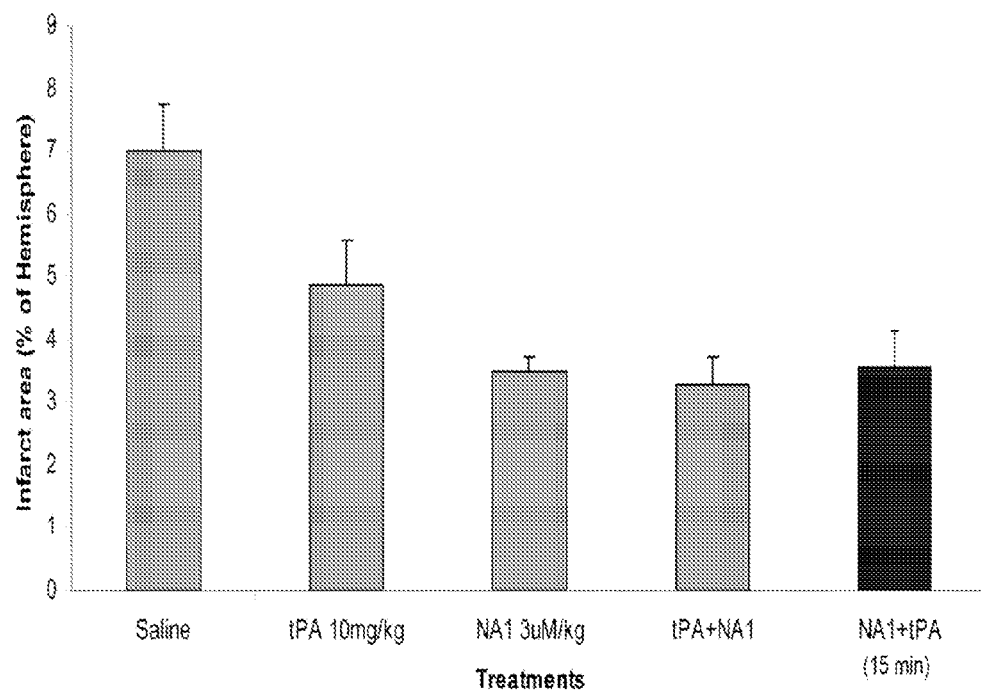
FIG. 11: Infarct areas in rat brains 24 hours after being subjected to a stroke and treated with various combinations and times of tPA and NA-1 (Tat-NR2B9c) dosing.

To demonstrate that Tat-NR2B9c and tPA could be given simultaneously in animal models of stroke, we again used the PIAL occlusion model of stroke in rats as above. Tat-NR2B9c was given as a 4-5 minute intravenous infusion 1 hour after the stroke, and tPA was given as prescribed in humans (10% of the dose by weight as a bolus followed by the remaining 90% of the dose given as an infusion over 1 hour) but with dose levels appropriate for rodent studies (10 times the human dose by weight). Groups (n=10) also included animals given both Tat-NR2B9c and tPA by these dose strategies concurrently, or with tPA initiated 15 minutes after the infusion of Tat-NR2B9c. FIG. 11 demonstrates that Tat-NR2B9c plus tPA is more effective than tPA alone when given either concurrently or when the Tat-NR2B9c dose precedes the tPA dose. Although the efficacy of the combined treatment in rats is similar to that of Tat-NR2B9c alone, the efficacy of the combined treatments probably reflects contributions of both tPA and Tat-NR2B9c because some of the Tat-NR2B9c is subject to cleavage as the result of tPA converting plasminogen to the protease plasmin, which is able to cleave Tat-NR2B9c in plasma. In other words, the data is consistent with activity lost as a result of Tat-NR2B9c being cleaved by plasmin being compensated for by tPA-mediated reperfusion. Cleavage of Tat-NR2B9c by plasmin is expected to occur to a lesser extent in humans than rats because the dose of tPA (by weight) for activation of plasminogen is ten-fold less in humans than rats. Thus, these data provide evidence that in humans the contribution of tPA can combined with that of Tat-NR2B9c in reducing damaging effects of stroke or other ischemic to the CNS with greater effect than either agent alone.

Although the invention has been described in detail for purposes of clarity of understanding, it will be obvious that certain modifications may be practiced within the scope of the appended claims. All publications, accession numbers, and patent documents cited in this application are hereby incorporated by reference in their entirety for all purposes to the same extent as if each were so individually denoted. To the extent more than one sequence is associated with an accession number at different times, the sequences associated with the accession number as of the effective filing date of this application is meant. The effective filing date is the date of the earliest priority application disclosing the accession number in question. Unless otherwise apparent from the context any element, embodiment, step, feature or aspect of the invention can be performed in combination with any other.

What is claimed is:

1. A method of treating a damaging effect of ischemia on the central nervous system, comprising
administering a PSD-95 inhibitor to a gyrencephalic primate having or at risk of ischemia, and performing reperfusion therapy on the primate, wherein the PSD-95 inhibitor and reperfusion treat a damaging effect of the ischemia on the central nervous system of the primate, and wherein the reperfusion therapy is performed more than 4.5 hours after onset of ischemia.

2. The method of claim 1, wherein the PSD-95 inhibitor is administered before reperfusion therapy is performed.

3. The method of claim 1, wherein the PSD-95-inhibitor is administered to a primate at risk of ischemia before onset of ischemia and the reperfusion therapy is performed after onset of ischemia.

4. The method of claim 1, wherein the PSD-95-inhibitor is administered and reperfusion therapy is performed after onset of ischemia.

5. The method of claim 1, wherein the ischemia is cerebral ischemia.

6. The method of claim 1, wherein the primate has a stroke.

7. The method of claim 1, wherein the ischemia is cardiac, pulmonary or major limb ischemia affecting the central nervous system by inhibiting blood flow to or from the CNS.

8. The method of claim 1, wherein the primate is tested for presence of cerebral ischemia and/or absence of cerebral hemorrhage between administration of the PSD-95 inhibitor and performance of the reperfusion therapy.

9. The method of claim 1, wherein the primate is assessed for presence or risk of hemorrhage between administering the PSD-95 inhibitor and performance of the reperfusion therapy.

10. The method of claim 9, wherein the assessment includes performing a PET scan, CAT scan, MRI or reviewing the primate's medical history or the use of one or more biomarkers providing an indication of ischemia.

11. The method of claim 1, wherein the PSD-95-inhibitor is a peptide.

12. The method of claim 1, wherein the PSD-95-inhibitor is tat-NR2B9c.

13. The method of claim 1, wherein the reperfusion is performed by administering a thrombolytic agent.

14. The method of claim 13, wherein the thrombolytic agent is a plasminogen activator.

15. The method of claim 14, wherein the thrombolytic agent is tPA.

16. The method of claim 13, wherein the interval between administering PSD-95 and reperfusion therapy is 30 min to 6 hr.

17. The method of claim 13, wherein the thrombolytic agent is administered by localized administration to a site of impaired blood flow.

18. The method of claim 1, wherein the reperfusion therapy is mechanical reperfusion.

19. The method of claim 1, wherein the reperfusion therapy is performed more than 4.5 hours and less than 24 hours after onset of ischemia.

20. The method of claim 1, wherein the reperfusion therapy is performed after determining the primate qualifies for reperfusion based on lack of a completed infarction, an ischemic penumbra and lack of hemorrhage as shown by CT, MRI or PET analysis.

21. The method of claim 20, wherein the reperfusion therapy is performed at least 12 or at least 24 hours after onset of ischemia.

22. The method of claim 1, wherein the reperfusion therapy is performed 275-690 minutes after onset of ischemia.

23. The method of claim 11, wherein the peptide is linked to an internalization peptide or is lipidated thereby facilitating passage of the peptide across a cell membrane or the blood brain barrier.

24. The method of claim 23, wherein the peptide is a myristoylated peptide.

25. The method of claim 24, wherein peptide has an amino acid sequence consisting or comprising of KLSSIESDV (SEQ ID NO:5) or KLSSIETDV (SEQ ID NO:43).

26. The method of claim 25, wherein the myristoylation is at the N-terminus of the peptide.

27. The method of claim 20, performed on a population of primates presenting sign(s) and/or symptom(s) of ischemia, wherein the PSD-95 inhibitor is administered to all the primates and reperfusion therapy only to the primates qualifying for reperfusion therapy.

28. The method of claim 27, wherein the primates present sign(s) and/or symptom(s) of stroke and the determining includes performing a brain scan that distinguishes ischemic stroke and hemorrhagic stroke and primates having ischemic stroke receive the reperfusion therapy and primates having hemorrhagic stroke do not.

* * * * *

SEQUENCE LISTING

```
<160> NUMBER OF SEQ ID NOS: 77

<210> SEQ ID NO 1
<211> LENGTH: 10
<212> TYPE: PRT
<213> ORGANISM: Artificial Sequence
<220> FEATURE:
<223> OTHER INFORMATION: Synthesized

<400> SEQUENCE: 1

Gly Arg Lys Lys Arg Arg Gln Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthesized

<400> SEQUENCE: 2

Tyr Gly Arg Lys Lys Arg Arg Gln Arg Arg Arg
1               5                   10

<210> SEQ ID NO 3
<211> LENGTH: 11
```

```
<212> TYPE: PRT
<213> ORGANISM: Artificial Sequence
<220> FEATURE:
<223> OTHER INFORMATION: Synthesized

<400> SEQUENCE: 3

Phe Gly Arg Lys Lys Arg Arg Gln Arg Arg
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Synthesized

<400> SEQUENCE: 4

Gly Arg Lys Lys Arg Arg Gln Arg Arg Pro Gln
 1               5                  10

<210> SEQ ID NO 5
<211> LENGTH: 9
<212> TYPE: PRT
<213> ORGANISM: Artificial Sequence
<220> FEATURE:
<223> OTHER INFORMATION: Synthesized

<400> SEQUENCE: 5

Lys Leu Ser Ser Ile Glu Ser Asp Val
 1               5

<210> SEQ ID NO 6
<211> LENGTH: 20
<212> TYPE: PRT
<213> ORGANISM: Artificial Sequence
<220> FEATURE:
<223> OTHER INFORMATION: Synthesized

<400> SEQUENCE: 6

Tyr Gly Arg Lys Lys Arg Arg Gln Arg Arg Lys Leu Ser Ser Ile
 1               5                  10                  15

Glu Ser Asp Val
             20

<210> SEQ ID NO 7
<211> LENGTH: 4
<212> TYPE: PRT
<213> ORGANISM: Artificial Sequence
<220> FEATURE:
<223> OTHER INFORMATION: Synthesized

<400> SEQUENCE: 7

Gly Leu Gly Phe
 1

<210> SEQ ID NO 8
<211> LENGTH: 22
<212> TYPE: PRT
<213> ORGANISM: Artificial Sequence
<220> FEATURE:
<223> OTHER INFORMATION: Synthesized

<400> SEQUENCE: 8

Val Asp Ser Glu Ile Ser Ser Leu Lys Arg Arg Gln Arg Arg Lys
 1               5                  10                  15

Lys Arg Gly Tyr Ile Asn
```

```
                    20

<210> SEQ ID NO 9
<211> LENGTH: 20
<212> TYPE: PRT
<213> ORGANISM: Artificial Sequence
<220> FEATURE:
<223> OTHER INFORMATION: Synthesized

<400> SEQUENCE: 9

Tyr Gly Arg Lys Lys Arg Arg Gln Arg Arg Lys Leu Ser Ser Ile
 1               5                  10                  15

Glu Ala Asp Ala
            20

<210> SEQ ID NO 10
<211> LENGTH: 10
<212> TYPE: PRT
<213> ORGANISM: Artificial Sequence
<220> FEATURE:
<223> OTHER INFORMATION: Synthesized

<400> SEQUENCE: 10

Arg Arg Arg Gln Arg Arg Lys Lys Arg Gly
 1               5                  10

<210> SEQ ID NO 11
<211> LENGTH: 20
<212> TYPE: PRT
<213> ORGANISM: Artificial Sequence
<220> FEATURE:
<223> OTHER INFORMATION: Synthesized

<400> SEQUENCE: 11

Phe Asn Gly Ser Ser Asn Gly His Val Tyr Glu Lys Leu Ser Ser Ile
 1               5                  10                  15

Glu Ser Asp Val
            20

<210> SEQ ID NO 12
<211> LENGTH: 4
<212> TYPE: PRT
<213> ORGANISM: Artificial Sequence
<220> FEATURE:
<223> OTHER INFORMATION: Synthesized

<400> SEQUENCE: 12

Glu Ser Asp Val
 1

<210> SEQ ID NO 13
<211> LENGTH: 20
<212> TYPE: PRT
<213> ORGANISM: Artificial Sequence
<220> FEATURE:
<223> OTHER INFORMATION: Synthesized

<400> SEQUENCE: 13

His Pro Thr Asp Ile Thr Gly Pro Leu Asn Leu Ser Asp Pro Ser Val
 1               5                  10                  15

Ser Thr Val Val
            20

<210> SEQ ID NO 14
<211> LENGTH: 20
```

```
<212> TYPE: PRT
<213> ORGANISM: Artificial Sequence
<220> FEATURE:
<223> OTHER INFORMATION: Synthesized

<400> SEQUENCE: 14

Arg Arg Ala Ile Glu Arg Glu Glu Gly Gln Leu Gln Leu Cys Ser Arg
 1               5                  10                  15

His Arg Glu Ser
            20

<210> SEQ ID NO 15
<211> LENGTH: 20
<212> TYPE: PRT
<213> ORGANISM: Artificial Sequence
<220> FEATURE:
<223> OTHER INFORMATION: Synthesized

<400> SEQUENCE: 15

Thr Gln Gly Phe Pro Gly Pro Cys Thr Trp Arg Arg Ile Ser Ser Leu
 1               5                  10                  15

Glu Ser Glu Val
            20

<210> SEQ ID NO 16
<211> LENGTH: 20
<212> TYPE: PRT
<213> ORGANISM: Artificial Sequence
<220> FEATURE:
<223> OTHER INFORMATION: Synthesized

<400> SEQUENCE: 16

Ala Val Ser Arg Lys Thr Glu Leu Glu Glu Tyr Gln Arg Thr Ser Arg
 1               5                  10                  15

Thr Cys Glu Ser
            20

<210> SEQ ID NO 17
<211> LENGTH: 20
<212> TYPE: PRT
<213> ORGANISM: Artificial Sequence
<220> FEATURE:
<223> OTHER INFORMATION: Synthesized

<400> SEQUENCE: 17

Leu Asn Ser Cys Ser Asn Arg Arg Val Tyr Lys Lys Met Pro Ser Ile
 1               5                  10                  15

Glu Ser Asp Val
            20

<210> SEQ ID NO 18
<211> LENGTH: 20
<212> TYPE: PRT
<213> ORGANISM: Artificial Sequence
<220> FEATURE:
<223> OTHER INFORMATION: Synthesized

<400> SEQUENCE: 18

Gly Gly Asp Leu Gly Thr Arg Arg Gly Ser Ala His Phe Ser Ser Leu
 1               5                  10                  15

Glu Ser Glu Val
            20

<210> SEQ ID NO 19
```

```
<211> LENGTH: 20
<212> TYPE: PRT
<213> ORGANISM: Artificial Sequence
<220> FEATURE:
<223> OTHER INFORMATION: Synthesized

<400> SEQUENCE: 19

Gln Pro Thr Pro Thr Leu Gly Leu Asn Leu Gly Asn Asp Pro Asp Arg
1               5                   10                  15

Gly Thr Ser Ile
            20

<210> SEQ ID NO 20
<211> LENGTH: 20
<212> TYPE: PRT
<213> ORGANISM: Artificial Sequence
<220> FEATURE:
<223> OTHER INFORMATION: Synthesized

<400> SEQUENCE: 20

Met Gln Ser Ile Pro Cys Met Ser His Ser Ser Gly Met Pro Leu Gly
1               5                   10                  15

Ala Thr Gly Leu
            20

<210> SEQ ID NO 21
<211> LENGTH: 20
<212> TYPE: PRT
<213> ORGANISM: Artificial Sequence
<220> FEATURE:
<223> OTHER INFORMATION: Synthesized

<400> SEQUENCE: 21

Gln Asn Phe Ala Thr Tyr Lys Glu Gly Tyr Asn Val Tyr Gly Ile Glu
1               5                   10                  15

Ser Val Lys Ile
            20

<210> SEQ ID NO 22
<211> LENGTH: 20
<212> TYPE: PRT
<213> ORGANISM: Artificial Sequence
<220> FEATURE:
<223> OTHER INFORMATION: Synthesized

<400> SEQUENCE: 22

Gln Asn Tyr Ala Thr Tyr Arg Glu Gly Tyr Asn Val Tyr Gly Thr Glu
1               5                   10                  15

Ser Val Lys Ile
            20

<210> SEQ ID NO 23
<211> LENGTH: 20
<212> TYPE: PRT
<213> ORGANISM: Artificial Sequence
<220> FEATURE:
<223> OTHER INFORMATION: Synthesized

<400> SEQUENCE: 23

His Thr Gly Thr Ala Ile Arg Gln Ser Ser Gly Leu Ala Val Ile Ala
1               5                   10                  15

Ser Asp Leu Pro
            20
```

```
<210> SEQ ID NO 24
<211> LENGTH: 20
<212> TYPE: PRT
<213> ORGANISM: Artificial Sequence
<220> FEATURE:
<223> OTHER INFORMATION: Synthesized

<400> SEQUENCE: 24

Ser Phe Thr Ser Ile Leu Thr Cys His Gln Arg Arg Thr Gln Arg Lys
 1               5                  10                  15

Glu Thr Val Ala
            20

<210> SEQ ID NO 25
<211> LENGTH: 20
<212> TYPE: PRT
<213> ORGANISM: Artificial Sequence
<220> FEATURE:
<223> OTHER INFORMATION: Synthesized

<400> SEQUENCE: 25

Glu Val Ile Asn Met His Thr Phe Asn Asp Arg Arg Leu Pro Gly Lys
 1               5                  10                  15

Glu Thr Met Ala
            20

<210> SEQ ID NO 26
<211> LENGTH: 11
<212> TYPE: PRT
<213> ORGANISM: Artificial Sequence
<220> FEATURE:
<223> OTHER INFORMATION: Synthesized

<400> SEQUENCE: 26

Arg Arg Arg Gln Arg Arg Lys Lys Arg Gly Tyr
 1               5                  10

<210> SEQ ID NO 27
<211> LENGTH: 4
<212> TYPE: PRT
<213> ORGANISM: Artificial Sequence
<220> FEATURE:
<223> OTHER INFORMATION: Synthesized

<400> SEQUENCE: 27

Ser Thr Val Val
 1

<210> SEQ ID NO 28
<211> LENGTH: 4
<212> TYPE: PRT
<213> ORGANISM: Artificial Sequence
<220> FEATURE:
<223> OTHER INFORMATION: Synthesized

<400> SEQUENCE: 28

His Arg Glu Ser
 1

<210> SEQ ID NO 29
<211> LENGTH: 4
<212> TYPE: PRT
<213> ORGANISM: Artificial Sequence
<220> FEATURE:
<223> OTHER INFORMATION: Synthesized

<400> SEQUENCE: 29
```

```
Glu Ser Glu Val
1

<210> SEQ ID NO 30
<211> LENGTH: 4
<212> TYPE: PRT
<213> ORGANISM: Artificial Sequence
<220> FEATURE:
<223> OTHER INFORMATION: Synthesized

<400> SEQUENCE: 30

Thr Cys Glu Ser
1

<210> SEQ ID NO 31
<211> LENGTH: 4
<212> TYPE: PRT
<213> ORGANISM: Artificial Sequence
<220> FEATURE:
<223> OTHER INFORMATION: Synthesized

<400> SEQUENCE: 31

Gly Thr Ser Ile
1

<210> SEQ ID NO 32
<211> LENGTH: 4
<212> TYPE: PRT
<213> ORGANISM: Artificial Sequence
<220> FEATURE:
<223> OTHER INFORMATION: Synthesized

<400> SEQUENCE: 32

Ala Thr Gly Leu
1

<210> SEQ ID NO 33
<211> LENGTH: 4
<212> TYPE: PRT
<213> ORGANISM: Artificial Sequence
<220> FEATURE:
<223> OTHER INFORMATION: Synthesized

<400> SEQUENCE: 33

Ser Val Lys Ile
1

<210> SEQ ID NO 34
<211> LENGTH: 4
<212> TYPE: PRT
<213> ORGANISM: Artificial Sequence
<220> FEATURE:
<223> OTHER INFORMATION: Synthesized

<400> SEQUENCE: 34

Ser Asp Leu Pro
1

<210> SEQ ID NO 35
<211> LENGTH: 4
<212> TYPE: PRT
<213> ORGANISM: Artificial Sequence
<220> FEATURE:
<223> OTHER INFORMATION: Synthesized

<400> SEQUENCE: 35
```

```
Glu Thr Val Ala
1

<210> SEQ ID NO 36
<211> LENGTH: 4
<212> TYPE: PRT
<213> ORGANISM: Artificial Sequence
<220> FEATURE:
<223> OTHER INFORMATION: Synthesized

<400> SEQUENCE: 36

Glu Thr Met Ala
1

<210> SEQ ID NO 37
<211> LENGTH: 20
<212> TYPE: PRT
<213> ORGANISM: Artificial Sequence
<220> FEATURE:
<223> OTHER INFORMATION: Synthesized

<400> SEQUENCE: 37

Arg Arg Arg Gln Arg Arg Lys Lys Arg Gly Tyr Lys Leu Ser Ser Ile
1               5                   10                  15

Glu Thr Asp Val
            20

<210> SEQ ID NO 38
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = E, D, N, or Q
<220> FEATURE:
<221> NAME/KEY: VARIANT
<222> LOCATION: 2
<223> OTHER INFORMATION: Xaa = S or T
<220> FEATURE:
<221> NAME/KEY: VARIANT
<222> LOCATION: 3
<223> OTHER INFORMATION: Xaa = D, E, Q, or N
<220> FEATURE:
<221> NAME/KEY: VARIANT
<222> LOCATION: 4
<223> OTHER INFORMATION: Xaa = V or L

<400> SEQUENCE: 38

Xaa Xaa Xaa Xaa
1

<210> SEQ ID NO 39
<211> LENGTH: 4
<212> TYPE: PRT
<213> ORGANISM: Artificial Sequence
<220> FEATURE:
<223> OTHER INFORMATION: Synthesized

<400> SEQUENCE: 39

Glu Thr Asp Val
1

<210> SEQ ID NO 40
<211> LENGTH: 4
<212> TYPE: PRT
<213> ORGANISM: Artificial Sequence
```

```
<220> FEATURE:
<223> OTHER INFORMATION: Synthesized

<400> SEQUENCE: 40

Glu Thr Glu Val
 1

<210> SEQ ID NO 41
<211> LENGTH: 4
<212> TYPE: PRT
<213> ORGANISM: Artificial Sequence
<220> FEATURE:
<223> OTHER INFORMATION: Synthesized

<400> SEQUENCE: 41

Asp Thr Asp Val
 1

<210> SEQ ID NO 42
<211> LENGTH: 4
<212> TYPE: PRT
<213> ORGANISM: Artificial Sequence
<220> FEATURE:
<223> OTHER INFORMATION: Synthesized

<400> SEQUENCE: 42

Asp Thr Glu Val
 1

<210> SEQ ID NO 43
<211> LENGTH: 9
<212> TYPE: PRT
<213> ORGANISM: Artificial Sequence
<220> FEATURE:
<223> OTHER INFORMATION: Synthesized

<400> SEQUENCE: 43

Lys Leu Ser Ser Ile Glu Thr Asp Val
 1               5

<210> SEQ ID NO 44
<211> LENGTH: 5
<212> TYPE: PRT
<213> ORGANISM: Artificial Sequence
<220> FEATURE:
<223> OTHER INFORMATION: Synthesized

<400> SEQUENCE: 44

Gly Ser Ser Ser Ser
 1               5

<210> SEQ ID NO 45
<211> LENGTH: 5
<212> TYPE: PRT
<213> ORGANISM: Artificial Sequence
<220> FEATURE:
<223> OTHER INFORMATION: Synthesized

<400> SEQUENCE: 45

Thr Gly Glu Lys Pro
 1               5

<210> SEQ ID NO 46
<211> LENGTH: 8
<212> TYPE: PRT
<213> ORGANISM: Artificial Sequence
<220> FEATURE:
```

```
<223> OTHER INFORMATION: Synthesized

<400> SEQUENCE: 46

Gly Gly Arg Arg Gly Gly Gly Ser
 1               5

<210> SEQ ID NO 47
<211> LENGTH: 9
<212> TYPE: PRT
<213> ORGANISM: Artificial Sequence
<220> FEATURE:
<223> OTHER INFORMATION: Synthesized

<400> SEQUENCE: 47

Leu Arg Gln Arg Asp Gly Glu Arg Pro
 1               5

<210> SEQ ID NO 48
<211> LENGTH: 13
<212> TYPE: PRT
<213> ORGANISM: Artificial Sequence
<220> FEATURE:
<223> OTHER INFORMATION: Synthesized

<400> SEQUENCE: 48

Tyr Gly Arg Lys Lys Arg Arg Gln Arg Arg Pro Gln
 1               5                  10

<210> SEQ ID NO 49
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or an amino acid that is not Y

<400> SEQUENCE: 49

Xaa Gly Arg Lys Lys Arg Arg Gln Arg Arg Arg
 1               5                  10

<210> SEQ ID NO 50
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 50

Xaa Gly Lys Lys Lys Lys Lys Gln Lys Lys Lys
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid
```

```
<400> SEQUENCE: 51

Xaa Arg Lys Lys Arg Arg Gln Arg Arg Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 52

Xaa Gly Ala Lys Lys Arg Arg Gln Arg Arg Arg
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 53

Xaa Ala Lys Lys Arg Arg Gln Arg Arg Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 54

Xaa Gly Arg Lys Ala Arg Arg Gln Arg Arg Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 55

Xaa Arg Lys Ala Arg Arg Gln Arg Arg Arg
1               5                   10

<210> SEQ ID NO 56
<211> LENGTH: 11
<212> TYPE: PRT
<213> ORGANISM: Artificial Sequence
<220> FEATURE:
```

```
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 56

Xaa Gly Arg Lys Lys Ala Arg Gln Arg Arg
 1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 57

Xaa Arg Lys Lys Ala Arg Gln Arg Arg
 1               5

<210> SEQ ID NO 58
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 58

Xaa Gly Arg Lys Lys Arg Arg Gln Ala Arg Arg
 1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 59

Xaa Arg Lys Lys Arg Arg Gln Ala Arg Arg
 1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 60

Xaa Gly Arg Lys Lys Arg Arg Gln Arg Ala Arg
 1               5                   10
```

```
<210> SEQ ID NO 61
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 61

Xaa Arg Lys Lys Arg Arg Gln Arg Ala Arg
 1               5                  10

<210> SEQ ID NO 62
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 62

Xaa Arg Arg Pro Arg Arg Pro Arg Arg Pro Arg Arg
 1               5                  10

<210> SEQ ID NO 63
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 63

Xaa Arg Arg Ala Arg Arg Ala Arg Arg Ala Arg Arg
 1               5                  10

<210> SEQ ID NO 64
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 64

Xaa Arg Arg Arg Ala Arg Arg Arg Ala Arg Arg
 1               5                  10

<210> SEQ ID NO 65
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid
```

<400> SEQUENCE: 65

Xaa Arg Arg Arg Pro Arg Arg Pro Arg Arg
 1               5                   10

<210> SEQ ID NO 66
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 66

Xaa Arg Arg Pro Arg Arg Pro Arg Arg
 1               5

<210> SEQ ID NO 67
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 67

Xaa Arg Arg Ala Arg Arg Ala Arg Arg
 1               5

<210> SEQ ID NO 68
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = E, Q, A, or an analog therof
<220> FEATURE:
<221> NAME/KEY: VARIANT
<222> LOCATION: 2
<223> OTHER INFORMATION: Xaa = T or S
<220> FEATURE:
<221> NAME/KEY: VARIANT
<222> LOCATION: 3
<223> OTHER INFORMATION: Xaa = A, Q, D, N, N-Me-A, N-Me-Q, N-Me-D,
      N-Me-N, or an analogue thereof

<400> SEQUENCE: 68

Xaa Xaa Xaa Val
 1

<210> SEQ ID NO 69
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 1
<223> OTHER INFORMATION: Xaa = Blank or any amino acid

<400> SEQUENCE: 69

```
Xaa Phe Gly Arg Lys Lys Arg Gln Arg Arg
1               5                   10

<210> SEQ ID NO 70
<211> LENGTH: 20
<212> TYPE: PRT
<213> ORGANISM: Artificial Sequence
<220> FEATURE:
<223> OTHER INFORMATION: Synthesized

<400> SEQUENCE: 70

Arg Arg Arg Gln Arg Arg Lys Lys Arg Gly Tyr Lys Leu Ser Ser Ile
1               5                   10                  15

Glu Ser Asp Val
            20

<210> SEQ ID NO 71
<211> LENGTH: 5
<212> TYPE: PRT
<213> ORGANISM: Artificial Sequence
<220> FEATURE:
<223> OTHER INFORMATION: Synthesized

<400> SEQUENCE: 71

Ile Glu Ser Asp Val
1               5

<210> SEQ ID NO 72
<211> LENGTH: 11
<212> TYPE: PRT
<213> ORGANISM: Artificial Sequence
<220> FEATURE:
<223> OTHER INFORMATION: Synthesized

<400> SEQUENCE: 72

Gly Arg Lys Lys Arg Arg Gln Arg Arg Arg Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthesized

<400> SEQUENCE: 73

Ile Glu Thr Asp Val
1               5

<210> SEQ ID NO 74
<211> LENGTH: 5
<212> TYPE: PRT
<213> ORGANISM: Artificial Sequence
<220> FEATURE:
<223> OTHER INFORMATION: Synthesized

<400> SEQUENCE: 74

Ile Glu Thr Ala Val
1               5

<210> SEQ ID NO 75
<211> LENGTH: 9
<212> TYPE: PRT
<213> ORGANISM: Artificial Sequence
<220> FEATURE:
<223> OTHER INFORMATION: Synthesized
```

```
<400> SEQUENCE: 75

Arg Arg Arg Gln Arg Arg Lys Lys Arg
 1               5

<210> SEQ ID NO 76
<211> LENGTH: 9
<212> TYPE: PRT
<213> ORGANISM: Artificial Sequence
<220> FEATURE:
<223> OTHER INFORMATION: Synthesized

<400> SEQUENCE: 76

Lys Leu Ser Ser Ile Glu Ala Asp Ala
 1               5

<210> SEQ ID NO 77
<211> LENGTH: 14
<212> TYPE: PRT
<213> ORGANISM: Artificial Sequence
<220> FEATURE:
<223> OTHER INFORMATION: Synthesized

<400> SEQUENCE: 77

Arg Leu Ser Gly Met Asn Glu Val Leu Ser Phe Arg Trp Leu
 1               5                  10
```